United States Patent
Hsu

(10) Patent No.: US 10,537,608 B2
(45) Date of Patent: *Jan. 21, 2020

(54) ADIPONECTIN PEPTIDOMIMETICS FOR TREATING OCULAR DISORDERS

(71) Applicant: Allysta Pharmaceuticals, Inc., Belmont, CA (US)

(72) Inventor: Henry Hsu, Belmont, CA (US)

(73) Assignee: ALLYSTA PHARMACEUTICALS, INC., San Mateo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/676,968

(22) Filed: Aug. 14, 2017

(65) Prior Publication Data

US 2018/0078616 A1 Mar. 22, 2018

Related U.S. Application Data

(63) Continuation-in-part of application No. PCT/US2016/030142, filed on Apr. 29, 2016.

(60) Provisional application No. 62/156,127, filed on May 1, 2015.

(51) Int. Cl.

| | |
|---|---|
| *A61K 38/08* | (2019.01) |
| *C07K 7/06* | (2006.01) |
| *C07K 14/47* | (2006.01) |
| *C07K 14/575* | (2006.01) |
| *A61P 27/02* | (2006.01) |
| *A61K 45/06* | (2006.01) |
| *A61K 31/4725* | (2006.01) |
| *A61K 38/22* | (2006.01) |
| *A61K 38/00* | (2006.01) |
| *A61K 38/13* | (2006.01) |
| *A61K 9/00* | (2006.01) |

(52) U.S. Cl.
CPC .......... *A61K 38/08* (2013.01); *A61K 31/4725* (2013.01); *A61K 38/22* (2013.01); *A61K 45/06* (2013.01); *A61P 27/02* (2018.01); *C07K 7/06* (2013.01); *C07K 14/47* (2013.01); *C07K 14/5759* (2013.01); *A61K 9/0048* (2013.01); *A61K 38/00* (2013.01); *A61K 38/13* (2013.01)

(58) Field of Classification Search
CPC ................ A61K 38/13; A61K 2300/00; A61K 31/4725; A61K 38/00; A61K 38/08; A61K 38/22; A61K 45/06; A61K 9/0048; A61P 27/02; C07K 14/47; C07K 14/5759; C07K 7/06

See application file for complete search history.

(56) References Cited

U.S. PATENT DOCUMENTS

| | | | | |
|---|---|---|---|---|
| 8,815,795 | B2* | 8/2014 | Yoon | A61K 38/22 514/1.1 |
| 9,750,636 | B2* | 9/2017 | Rubin | A61F 9/0017 |
| 2014/0057833 | A1* | 2/2014 | Otvos | C07K 14/5759 514/1.9 |
| 2018/0161390 | A1* | 6/2018 | Hsu | C07K 14/5759 |

FOREIGN PATENT DOCUMENTS

WO 2016179007 A1 11/2016

OTHER PUBLICATIONS

Sheppard et al. Lifitegrast Ophthalmic Solution 5.0% for Treatment of Dry Eye Disease. Ophthalmology, Feb. 2014. vol. 121, No. 2, pp. 475-483. (Year: 2014).*
Li et al. Therapeutic Effect of Topical Adiponectin in a Mouse Model of Desiccating Stress-Induced Dry Eye. Investigative Ophthalmology and Visual Science, Jan. 2013, vol. 54, No. 1, pp. 155-162. (Year: 2013).*
International Search Report and Written Opinion on PCT/US18/45527, dated Oct. 16, 2018, 3 pages.

* cited by examiner

*Primary Examiner* — Marcela M Cordero Garcia
(74) *Attorney, Agent, or Firm* — Yong Chen; Lin Sun-Hoffman; Liu Chen & Hoffman LLP

(57) ABSTRACT

Provided herein are compositions and methods for treating dry eye or an ocular disease associated with inflammation in a subject in need thereof. The therapeutic compositions comprise an adiponectin peptidomimetic compound, and a pharmaceutically acceptable carrier, and administering a therapeutic agent. Also provided are methods for alleviating one or more symptoms or clinical signs of dry eye or an ocular disease associated with inflammation in a subject in need thereof.

16 Claims, 7 Drawing Sheets
Specification includes a Sequence Listing.

* p< 0.05%

* $p < 0.05\%$

FIG. 6A  UT  11.09%
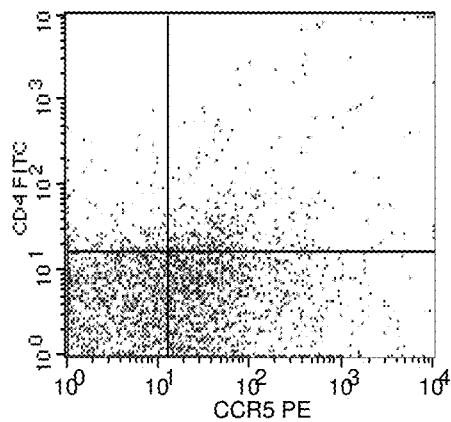
FIG. 6B  BSS  23.56%
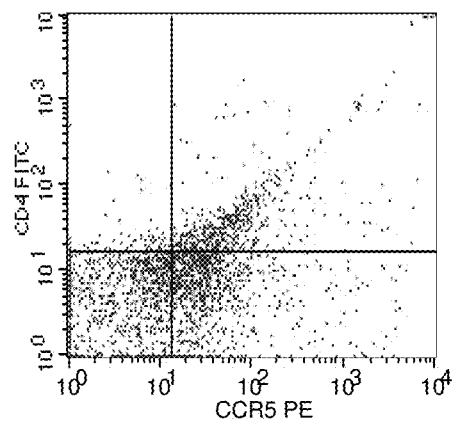
FIG. 6C
0.1% ADP355  15.16%
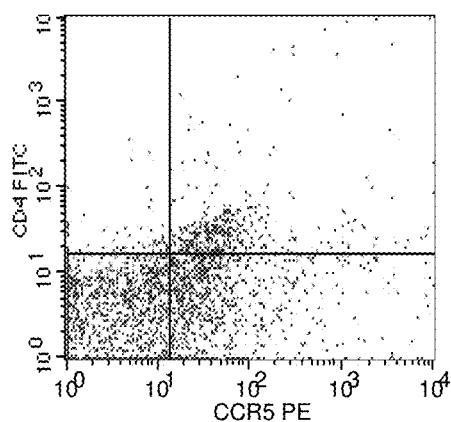
FIG. 6D
5% Lifitegrast  17.44%
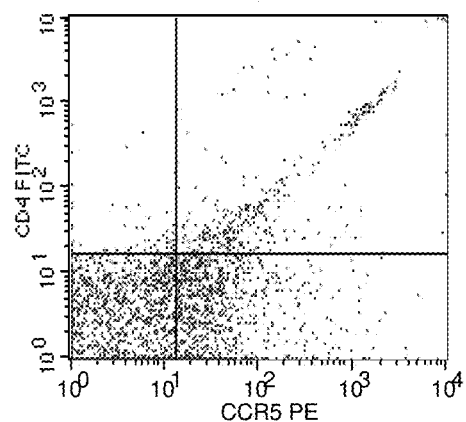
FIG. 6E
0.1%ADP355 + 5%Lifitegrast 12.53%
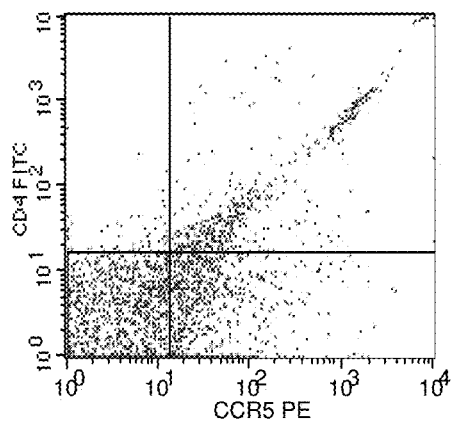

FIG. 7

| Tissue | Treatment | Cytokine (pg/ml) | | | |
|---|---|---|---|---|---|
| | | IFN-γ | IL-1β | MIP-1β | TNF-α |
| Conjunctiva | UT-Untreated | 26.235 | 0.422 | 1.053 | 0.110 |
| | BSS-vehicle | 48.620 | 1.836 | 5.811 | 2.441 |
| | ADP 355 (0.1%) | 35.422 | 1.684 | 2.183 | 1.147 |
| | Lifitegrast (5%) | 38.735 | 1.836 | 3.125 | 1.300 |
| | ADP355 + Lifitegrast | 32.124 | 1.760 | 2.218 | 0.442 |
| Lacrimal gland | UT-Untreated | 11.402 | 1.535 | 19.052 | non-detectable |
| | BSS-Vehicle | 19.483 | 5.343 | 77.097 | 6.873 |
| | ADP 355 (0.1%) | 16.973 | 5.101 | 54.338 | 3.280 |
| | Lifitegrast (5%) | 16.756 | 5.556 | 61.182 | 3.110 |
| | ADP355 + Lifitegrast | 15.881 | 4.312 | 44.726 | 2.941 |

SEQUENCE LISTING

```
<160> NUMBER OF SEQ ID NOS: 7

<210> SEQ ID NO 1
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 may be Asn or a non-natural
      amino acid
<220> FEATURE:
<221> NAME/KEY: MISC_FEATURE
<222> LOCATION: (1)..(11)
<223> OTHER INFORMATION: provided that at least one of positions 1, 4,
      7 or 10 is a non-natural amino acid
<220> FEATURE:
<221> NAME/KEY: MISC_FEATURE
<222> LOCATION: (4)..(4)
<223> OTHER INFORMATION: Xaa at position 4 may be Gly or a non-natural
      amino acid
<220> FEATURE:
<221> NAME/KEY: MISC_FEATURE
<222> LOCATION: (7)..(7)
<223> OTHER INFORMATION: Xaa at position 7 may be Tyr or a non-natural
      amino acid
<220> FEATURE:
<221> NAME/KEY: MISC_FEATURE
<222> LOCATION: (10)..(11)
<223> OTHER INFORMATION: when Xaa at position 10 or Xaa at position 11
      is a C-terminal
      amino acid, said C-terminal amino acid is optionally amidated
<220> FEATURE:
<221> NAME/KEY: MISC_FEATURE
<222> LOCATION: (10)..(10)
<223> OTHER INFORMATION: Xaa at position 10 may be Tyr or a non-natural
      amino acid
<220> FEATURE:
<221> NAME/KEY: MISC_FEATURE
```

```
<222> LOCATION: (11)..(11)
<223> OTHER INFORMATION: Xaa at position 11 may be absent, bAla or
      bAlaNH2

<400> SEQUENCE: 1

Xaa Ile Pro Xaa Leu Tyr Xaa Phe Ala Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is Asn or a non-natural amino
      acid
<220> FEATURE:
<221> NAME/KEY: MISC_FEATURE
<222> LOCATION: (1)..(10)
<223> OTHER INFORMATION: provided that at least one of Xaa at position
      1, Xaa at position 4, Xaa at position 7 or Xaa at position 10 is a
      non-natural amino
      acid
<220> FEATURE:
<221> NAME/KEY: MISC_FEATURE
<222> LOCATION: (1)..(10)
<223> OTHER INFORMATION: wherein the C-terminal amino acid is optionally
      amidated
<220> FEATURE:
<221> NAME/KEY: MISC_FEATURE
<222> LOCATION: (4)..(4)
<223> OTHER INFORMATION: Xaa at position 4 is Gly or a non-natural amino
      acid
<220> FEATURE:
<221> NAME/KEY: MISC_FEATURE
<222> LOCATION: (7)..(7)
<223> OTHER INFORMATION: Xaa at position 7 is Tyr or a non-natural amino
      acid
<220> FEATURE:
<221> NAME/KEY: MISC_FEATURE
<222> LOCATION: (10)..(10)
<223> OTHER INFORMATION: Xaa at position 10 is Tyr or a non-natural
      amino acid

<400> SEQUENCE: 2

Xaa Ile Pro Xaa Leu Tyr Xaa Phe Ala Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser

<400> SEQUENCE: 3
```

```
Xaa Ile Pro Xaa Leu Tyr Xaa Phe Ala Xaa
1               5                   10
```

<210> SEQ ID NO 4
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAla

<400> SEQUENCE: 4

```
Xaa Ile Pro Xaa Leu Tyr Xaa Phe Ala Xaa Xaa
1               5                   10
```

<210> SEQ ID NO 5
<211> LENGTH: 11
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 5

```
Xaa Ile Pro Xaa Leu Tyr Xaa Phe Ala Xaa Xaa
1               5                   10
```

<210> SEQ ID NO 6
<211> LENGTH: 10
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE

```
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser-NH2

<400> SEQUENCE: 6

Xaa Ile Pro Xaa Leu Tyr Xaa Phe Ala Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically synthesized peptide
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser

<400> SEQUENCE: 7

Xaa Ile Pro Xaa Leu Tyr Xaa Phe Ala Xaa His Pro
1               5                   10
```

ADIPONECTIN PEPTIDOMIMETICS FOR TREATING OCULAR DISORDERS

CROSS-REFERENCES TO RELATED APPLICATIONS

This application claims priority to and is a Continuation In Part of currently PCT Application No. PCT/US2016/030142, entitled, ADIPONECTIN PEPTIDOMIMETICS FOR TREATING OCULAR DISORDERS, naming Henry Hsu as inventor, filed Apr. 29, 2016, which published as WIPO Publication No. WO 2016/179007 on Nov. 10, 2016 and claims priority to U.S. Provisional Application No. 62/156,127. filed May 1, 2015, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED ON A COMPACT DISK

This application includes a Sequence Listing as a text file named "SEQLIST_098102-000110PC-1006637_ST25.txt" created Apr. 28, 2016, and containing 5,295 bytes. The material contained in this text file is incorporated by reference in its entirety for all purposes.

BACKGROUND OF THE INVENTION

The ocular surface system consists of the cornea, conjunctiva, lacrimal glands, meibomian glands, nasolacrimal duct, and their associated tear and connective tissue matrices, as well as the eyelids and eyelashes, all integrated by continuous epithelia and interconnected nervous, endocrine, immune, and vascular systems. Human tears are produced by the lacrimal glands. Tears are distributed by blinking, undergo evaporation from the ocular surface, and drain through the nasal lacrimal duct. Tears comprise three layers: an innermost layer of hydrophilic mucin, a slimy substance produced by the goblet cells that coats the ocular surface epithelium; an aqueous tear layer produced by the lacrimal glands which floats on the mucin layer and is approximately 0.9% saline; and a superficial thin lipid layer produced by the meibomian glands, which helps with uniform tear spreading and to slow down tear evaporation. This three-layer structure stabilizes the tear film and enables the tear film to keep the eye moist, create a smooth surface for light to pass through the eye, nourish the front of the eye, and provide protection from injury and infection. Factors that disturb the delicate homeostatic balance of the ocular surface system can adversely affect tear film stability and osmolarity, resulting in osmotic, mechanical, and inflammatory damage. Exposure of ocular surface epithelial cells to elevated tear osmolarity activates inflammatory pathways including the release of pro-inflammatory cytokines. This can lead to the recruitment and infiltration of immune cells to the ocular surface, particularly antigen presenting cells and T cells.

Dry eye disease (DED or dry eye), also known as keratoconjunctivitis sicca, is a multifactorial disorder of the tears and ocular surface. It is characterized by symptoms including dry irritated eyes, excessively watery eyes, burning and stinging, light sensitivity, a foreign body sensation, pain and redness, eye fatigue, and/or blurred vision. In dry eye the ocular surface epithelium undergoes squamous metaplasia, manifested by loss of goblet cells, mucin deficiency and keratinization, resulting in tear film instability. Factors that adversely affect tear film stability and osmolality can induce ocular surface damage and initiate an inflammatory cascade that generates innate and adaptive immune responses. These immuno-inflammatory responses lead to further ocular surface damage and the development of a self-perpetuating inflammatory cycle (Stevenson et al., Arch Ophthalmol. 2012, 130(i):90-100).

The major classes of dry eye are aqueous tear-deficient dry eye (ADDE) and evaporative dry eye (EDE). ADDE is due to failure of lacrimal tear secretion and this class can be further subdivided to Sjogren's syndrome dry eye (the lacrimal and salivary glands are targeted by an autoimmune process, e.g., rheumatoid arthritis) and non-Sjogren's syndrome dry eye (lacrimal dysfunction, but the systemic autoimmune features of Sjogren's syndrome are excluded, e.g., age-related dry eye). EDE is due to excessive water loss from the exposed ocular surface in the presence of normal lacrimal secretory function. Its causes can be intrinsic (due to intrinsic disease affecting lid structures or dynamics, e.g., meibomian gland dysfunction) or extrinsic (where ocular surface disease occurs due to some extrinsic exposure, e.g., vitamin A deficiency). With meibomian gland dysfunction, the lipid layer of tears is altered, causing increased tear evaporation. {See, e.g., "The Definition and Classification of Dry Eye Disease: Guidelines from the 2007 International Dry Eye Work Shop," Ocul Surf, 2007, 5(2): 75-92). In both classes of dry eye, the end result is a self-perpetuating cycle of irritation and inflammation.

It is estimated that almost 5 million Americans 50 years and older have DED, and millions more experience episodic symptoms of dry eye; of these, approximately two-thirds are women. The prevalence of DED rises dramatically with increasing age. Dry eye disease can hinder the performance of activities of daily living, and DED is associated with an overall decrease in quality of life.

There are several techniques or clinical measures used for diagnosing and evaluating the severity of a patient's dry eye, including the Ocular Surface Disease Index (OSDI) questionnaire, the Symptom Assessment in Dry Eye (SA DE), Tear Break-up Time (TBUT), vital dye staining of the ocular surface, tear meniscus height analysis, tear film osmolarity analysis, the Schirmer's Test, and the like. The TBUT test measures the time required for the three-layer tear film to break up. A shortened TBUT test time indicates a decreased quality of tears and is indicative of dry eye. The Schirmer's Test measures the volume of tears produced, and is performed by of placing a small strip of filter paper inside the lower eyelid (conjunctival sac) of each eye for several minutes, allowing tear fluid to be drawn into the filter paper by capillary action. The paper is then removed and the amount of moisture is measured in millimeters. Typically, a measurement of less than 5 mm indicates dry eye.

Ophthalmologists who treat chronic DED patients have to manage the symptoms of ocular surface inflammation. Apart from reducing vision, the symptoms of such inflammation also include redness, pain, swelling, edema (chemosis) of the conjunctiva and eyelids. In DED, the irritative symptoms may be due to the release of pro-inflammatory cytokines (Lam et al, Am J Ophthalmol, 2009, 147: 198-205; Albersmeyer et al., Exp Eye Res, 2010, 90(3):444-451) and infiltration of inflammatory cells (Kunert et al, Arch. Ophthalmol. 2000, 118-(11): 1489-96) on the ocular surface, as well as stimulation of the nerve fibers innervating the ocular surface, resulting ocular surface tissue damage. Inflammation also leads to epitheliopathy, the key clinical sign identified in DED.

Current therapies for dry eye are palliative with a focus on the replacement of tears to reduce symptoms. Conventional treatment of mild and moderate cases of dry eye includes supplemental lubrication. Application of ophthalmic formulations, such as therapeutic eye drops and artificial tears, every few hours can aid in maintaining and strengthening the tear film on the ocular surface and provide temporary relief. Lubricating tear ointments are also used. Tear ointments contain white petrolatum, mineral oil, and similar lubricants, and serve as a lubricant and an emollient. While these palliative therapies have benefits over the short term, they have limited utility in long-term control therapy for dry eye.

RESTASIS® (cyclosporine A) is the first prescription product for dry eye therapy. Cyclosporine A exerts immunosuppressive activity through several pathways and the immunomodulatory activity of cyclosporine A is used in the treatment of immune-based disorders, such as transplant rejection, psoriasis, ulcerative colitis, rheumatoid arthritis, and DED. Topical administration of cyclosporine A has been shown to increase tear fluid secretion, possibly by promoting the local release of parasympathetic nervous system-associated neurotransmitters. The beneficial effects of cyclosporine A treatment in DED are well established; however, it is clear that many patients with DED do not show a consistent therapeutic response to topical cyclosporine A.

Thus, there are currently few effective therapeutic options for the majority of patients with dry eye and ocular diseases associated with inflammation. As such, there is a high unmet need for effective and safe therapies. The present invention satisfies this need and provides other advantages as well.

BRIEF SUMMARY OF THE INVENTION

In one aspect, provided herein are compositions and methods for treating dry eye in a subject in need thereof. The method comprises administering to the subject a therapeutically effective amount of composition comprising: an adiponectin peptidomimetic compound and a Lifitegrast and a pharmaceutically acceptable carrier to treat dry eye in the subject.

In some embodiments, the composition and therapeutic agent are administered topically, by intravitreal injection, by subconjunctival injection, by conjunctival injection, by intramuscular injection, by subcutaneous injection, by intravenous injection, by intracameral injection, or by implantation into the subject's eye. In some embodiments, the dry eye is selected from the group consisting of hypolacrimation, tear deficiency, xerophthalmia, Sjogren's syndrome dry eye, non-Sjogren's syndrome dry eye, keratoconjuctivitis sicca, aqueous tear-deficiency dry eye (ADDE), evaporative dry eye (EDE), environmental dry eye, Stevens-Johnson syndrome, ocular pemphigoid, blepharitis marginal, eyelid-closure failure, sensory nerve paralysis, allergic conjunctivitis-associated dry eye, post-viral conjunctivitis dry eye, post-cataract surgery dry eye, VDT operation-associated dry eye, and contact lens wearing-associated dry eye.

In some instances, the composition and therapeutic agent are each administered to the subject once a day, two times a day, three times a day, four times a day, or more often (more frequently). In other instances, the composition and therapeutic agent are each administered every other day or less often (less frequently). In some embodiments, the adiponectin peptidomimetic compound is present in an amount between about 0.0001% (wt) to about 90% (wt) of the final composition. In some embodiments, the therapeutic agent is present in an amount between about 0.1% to about 20%. In some embodiments, the composition and therapeutic agent are each in a formulation selected from the group consisting of a solution, suspension, syrup, liquid, gel, hydrogel, emulsion, liposome, aerosol, mist, film, suspension, plug, polymer, implant, contact lens, ocular insert, nanoparticle, microparticle, a sustained release formulation, and a formulation suitable for an ocular medical device. In some embodiments the method further comprises administering a composition comprising cyclosporine, artificial tears, a corticosteroid, an anti-inflammatory agent, or any combination thereof.

In some embodiments, the adiponectin peptidomimetic compound is represented by Formula II: Xaai-Ile-Pro-Xaa$_2$-Leu-Tyr-Xaa$_3$-Phe-Ala-Xaa$_4$-Xaa$_5$ (SEQ ID NO:2) (II); wherein the C-terminal amino acid is optionally amidated; a variant thereof; a derivative thereof; or a pharmaceutically acceptable salt thereof. In some instances, the adiponectin peptidomimetic compound is selected from the group consisting of D-Asn-Ile-Pro-Nva-Leu-Tyr-D-Ser-Phe-Ala-D-Ser (SEQ ID NO:3), D-Asn-Ile-Pro-Nva-Leu-Tyr-D-Ser-Phe-Ala-D-Ser-p-Ala (SEQ ID NO:4), D-Asn-Ile-Pro-Nva-Leu-Tyr-D-Ser-Phe-Ala-D-Ser-p-Ala-NH$_2$ (SEQ ID NO:5), D-Asn-Ile-Pro-Nva-Leu-Tyr-D-Ser-Phe-Ala-D-Ser-NH$_2$ (SEQ ID NO:6), (D-Asn-Ile-Pro-Nva-Leu-Tyr-D-Ser-Phe-Ala-D-Ser-His-Pro)$_2$-Dab-NH$_2$ (SEQ ID NO:7), a variant thereof, a derivative thereof, and a pharmaceutically acceptable salt thereof, wherein Dab represents 2,3-diamino butyric acid). In some embodiments, the adiponectin peptidomimetic compound is ADP 355 (SEQ ID NO:6), or a pharmaceutically acceptable salt thereof.

In one embodiment, the therapeutic agent is selected from Lifitegrast and Restasis® or a pharmaceutically acceptable salt thereof. In some embodiments, the therapeutic agent comprises about 3.5% to about 6.5% Lifitegrast.

In another aspect, provided herein is a method for treating an ocular disease associated with inflammation in a subject in need thereof. The method comprises administering to the subject a therapeutically effective amount of a composition comprising an adiponectin peptidomimetic compound (SEQ ID NO:6) or a pharmaceutically acceptable salt thereof, and a pharmaceutically acceptable carrier, and administering a therapeutic agent to treat the ocular disease associated with inflammation in the subject.

In another aspect, provided herein is a method for alleviating at least one symptom or clinical sign of dry eye in a subject in need thereof. The method comprises administering to the subject a therapeutically effective amount of an adiponectin peptidomimetic compound (SEQ ID NO:6) or a pharmaceutically acceptable salt thereof and a pharmaceutically acceptable carrier; and administering a therapeutic agent to alleviate at least one symptom or clinical sign of dry eye in the subject.

In yet another aspect, provided herein is a method for treating an ocular disease or disorder in a subject in need thereof. The method comprises administering to the subject a therapeutically effective amount of an adiponectin peptidomimetic compound or a pharmaceutically acceptable salt thereof: and a pharmaceutically acceptable carrier; and administering a therapeutic agent to treat the ocular disease associated with inflammation in the subject.

In another aspect, the subject can present with at least one symptom or clinical sign of dry eye selected from the group consisting of a change in tear secretion, a change in tear clearance, ocular surface damage, corneal epithelial defects, a change in ocular surface cells, a change in tear film stability, a change in tear volume, a change in tear film composition, a change in tear osmolarity, and any combination thereof.

Other objects, features, and advantages of the present invention will be apparent to one of skill in the art from the following detailed description and figures.

BRIEF DESCRIPTION OF THE DRAWINGS

FIG. 3A after treating for 5 days. FIG. 3B, after 10 days treatment.

FIG. 4A, after treating for 5 days. FIG. 3B, after 10 days treatment.

FIG. 6B depicts scatter plots illustrating the change in activated T cell levels when dry eye presents in the lacrimal gland. FIG. 6A represents scatter plots of activated T cell level of normal (UT) eye. After treatment, the changes in activated T cell levels are illustrated in scatter plots of FIG. 6C (after administration of 0.1% ADP 355), FIG. 6D (after administration of 5% Lifitegrast), and FIG. 6E (after administration of both 0.1% ADP 355+Lifitegrast 5%).

FIG. 7 is table of cytokine levels identified in both the conjunctiva and lacrimal gland of normal (UT) and dry eyes with and without therapeutic intervention.

DETAILED DESCRIPTION OF THE INVENTION

I. Introduction

Figure 1:
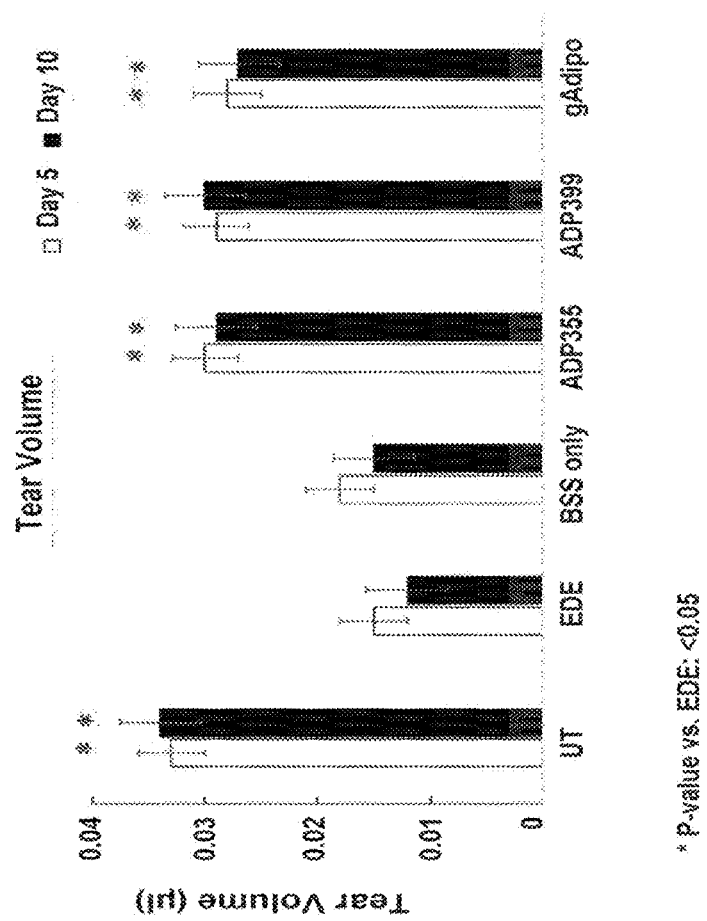
FIG. 1 illustrates that administration of an adiponectin peptidomimetic to a mouse model of experimental dry eye (EDE) increased tear volume compared to control untreated EDE mice. Tear volumes were measured at day 5 and day 10 after treatment initiation. Tear volumes in the adiponectin peptidomimetic-treated animals were similar to that of untreated normal mice. Also, tear volume was significantly improved in the treated EDE mice compared to control untreated EDE mice. "UT" represents untreated (normal) mice; "EDE" represents untreated experimental dry eye control mice; "BSS only" represents experimental dry eye mice treated with only balanced salt solution; "ADP355" represents experimental dry eye mice treated with adiponectin peptidomimetic; "ADP399" represents experimental dry eye mice treated with adiponectin peptidomimetic (linear branched dimer); and "gAdipo" represents experimental dry eye mice treated with recombinant murine full-length globular adiponectin.

Provided herein are compositions, methods and kits for treating dry eye or an ocular disease associated with inflammation in a subject in need thereof. The method includes administering to said subject a therapeutically effective composition comprising an adiponectin peptidomimetic compound or a pharmaceutically acceptable salt thereof, and a pharmaceutically acceptable carrier and administering a therapeutic agent. Also provided herein are methods for alleviating at least one symptom or clinical sign of dry eye in a subject. In some embodiments, the therapeutically effective composition comprises at least two different adiponectin peptidomimetic compounds or pharmaceutically acceptable salts thereof and administering a therapeutic agent. The invention is based, in part, on the discovery that administration to the eye of an adiponectin peptidomimetic compound or a pharmaceutically acceptable salt thereof and administering a therapeutic agent increases tear volume and reduces corneal surface irregularities in subjects with dry eye.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "dry eye" refers to a multifactorial disease of the tears and ocular surface (including the cornea, conjunctiva, and eye lids) results in symptoms of discomfort, visual disturbance and tear film instability with potential damage to the ocular surface, as defined by the "The Definition and Classification of Dry Eye Disease: Guidelines from the 2007 International Dry Eye Work Shop," Ocul Surf, 2007, 5(2): 75-92). Dry eye can be accompanied by increased osmolarity of the tear film and inflammation of the ocular surface. Dry eye includes dry eye syndrome, keratoconjunctivitis sicca (KCS), dysfunctional tear syndrome, lacrimal keratoconjunctivitis, evaporative tear deficiency, aqueous tear deficiency, and LASIK-induced neurotrophic epitheliopathy (LE).

The term "ocular disease associated with inflammation" refers to a disease or disorder of the eye wherein inflammation causes damage to the ocular surface system. As used herein, "the ocular surface system" includes the cornea, conjunctiva, lacrimal glands, meibomian glands, nasolacrimal duct, and their associated tear and connective tissue matrices, as well as the eyelids and eyelashes, all integrated by continuous epithelia and interconnected nervous, endocrine, immune, and vascular systems.

The term "a symptom" refers to a subjective indication or observation of a disorder or disease experienced or perceived by a patient.

The term "a clinical sign" refers to an objective indication, observation or evidence of a disorder or a disease that may be detected or interpreted by a clinician.

The term "adiponectin" refers to a polypeptide that is primarily derived from adipocytes. The adiponectin polypeptide is composed of 244 amino acid residues containing a short non-collagenous N-terminal segment (about 130 amino acids) followed by a collagenI like sequence (Maeda et al., BBRC, 1996, 221:286-289). The amino acid sequence of human adiponectin polypeptide is found, for example, in NCBI Ref. Sequence No. NP 004788.1 or UniPro Ref. No. Q15848. Adiponect n can form a homotrimer that is similar in size and overall structure to complement protein Clq, with particularly high homology (about 65-70% homology) to Clq in the C-terminal globular domain. This globular domain (about 130 amino acids) is believed to be essential for the biological activity of natural (native) adiponectin. The crystal structure of adiponectin revealed additional high structural similarity between this same globular domain and TNFa (about 60% homology).

The term "an adiponectin peptidomimetic" refers to a peptide compound that mimics the activity or function of adiponectin protein. An adiponectin peptidomimetic may have the ability to bind to or interact with one or more adiponectin receptors (AdipoRI and AdipoR2) or variants thereof. A peptidomimetic may be a backbone modified peptide, any polyamide or other polymeric structure resembling peptides, peptides containing non-natural amino acid residues or a peptide derivative.

The term "peptide" refers to an organic compound comprising a chain of two or more amino acids covalently joined by peptide bonds. Peptides may be referred to with respect to the number of constituent amino acids, i.e., a dipeptide contains two amino acid residues, a tripeptide contains three, etc.

The term "amino acid" as used herein means an organic compound containing both a basic amino group and an acidic carboxyl group. Included within this term are natural amino acids {e.g., L-amino acids), modified and unusual amino acids {e.g., D-amino acids), as well as amino acids which are known to occur biologically in free or combined form but usually do not occur in proteins. Included within this term are modified and unusual amino acids, such as those disclosed in, for example, Roberts and Vellaccio (1983) The Peptides, 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproine, tert-leucine, 4-aminocyclohexylalanine, N-methyl-norleucine, norvaline, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "hydrophobic residue" includes valine, isoleucine, leucine, methionine, phenylalanine, tyrosine, tryptophan, and functional equivalents thereof.

The term "polar residue" includes aspartic acid, asparagine, glutamic acid, glutamine, lysine, arginine, histidine, serine, and functional equivalents thereof.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the a-carbon of an a-amino acid).

The term "side chain" means groups that are attached to the peptide backbone, and typically refers to the group attached to the a-carbon of an .alpha. -amino acid. For example, for the side chains of the proteinogenic amino acids include: methyl (alanine), hydroxymethyl (swine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of the peptide, or the terminal amino or carboxyl groups, is modified to a derivative functional group. An amino group may be derivatized as an amide (such as an alkyl carboxamide, acetamide), a carbamate (such as an alkyl carbamate, e.g. methyl carbamate or t-butylcarbamate), or a urea. A hydroxyl group may be derivatized as an ester (such as an alkanoate, e.g. acetate, propionate, or an arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). A person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts of derivatives.

The term "non-natural amino acid" is used to refer to an amino acid which does not exist on its own in nature, but rather, has been synthesized or created by man. Examples of non-natural amino acids include iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, animohexanoic acid, telluromethionine, homoallylglycine, and homopropargylglycine. D-amino acids are also examples of non-natural amino acids.

"Nva" corresponds to the non-natural amino acid norvaline, also known as 2(L)-aminopentanoic acid. "NvaNH$_2$" corresponds to 2(L)-aminopentanamide. "Acp" corresponds to the non-natural amino acid 6-aminocaproic acid, also known as 6-amino-hexanoic acid. "Acp H$_2$" corresponds to 6-aminocapramide, also known as 6-amino-hexanamide. "Dpr(Ac)" corresponds to N2(3)-acetyl-diaminopropionic acid. "Dbu" corresponds to 2,4-diaminobutyric acid. "Glc" corresponds to glucose. "PGlc" corresponds to beta-glucose. "SerP(Glc)" corresponds to serine glycosylated with a beta-glucosyl residue on the alcohol hydroxyl group. "Thr(NAc-Gal)" corresponds to threonine glycosylated with an N-acetyl galactosaminyl residue on the alcohol hydroxyl group. "Tyr($I_2$)" corresponds to 3,5-diiodotyrosine. "N-MeArg" corresponds to N-methyl-arginine. "PAla" corresponds to beta-alanine, also known as 3-aminopropanoic acid. "PAla-$H_2$" corresponds to the amide derivative of beta-alanine, also known as 3-aminopropanamide. "(D)-Ser" corresponds to D-serine. "Apa" corresponds to aminopentanoic acid. "AlloThr" corresponds to allo-threonine, also known as (2S,3S)-2-amino-3-hydroxybutanoic acid. "3Hyp" corresponds to 3-hydroxyproline. "4Hyp" corresponds to 4-hydroxyproline.

As used herein, the term "hydroxylated acyclic amino acid" refers to an acyclic amino acid that contains at least one alcohol hydroxyl group in its structure. Preferred, but non-limiting, examples of hydroxylated acyclic amino acid are serine, (D)-serine, threonine, (D)-threonine, (L)-allo-threonine, (D)-allo-threonine, (L)-isoserine, (D)-isoserine, (i)-β-homoserine, (D)-P-homoserine, (L)-homoserine, and (D)-homoserine.

As used herein, the term "aliphatic amino acid" refers to an amino acid which carbon chain is aliphatic in nature. Non-limiting examples of aliphatic amino acids are alanine, arginine, asparagine, aspartic acid, cysteine, glutamic acid, glutamine, glycine, isoleucine, leucine, lysine, methionine, proline, serine, threonine, valine, Nva, Nva-$NH_2$, Acp, Acp-$NH_2$, Dpr(Ac), Abu, N-MeArg, pAla, pAla-$NH_2$, Apa, and AlloThr. Preferred aliphatic amino acids within the present application are pAla, pAla-$NH_2$, Acp and Acp-$NH_2$.

The term "peptide transduction domain" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

An "acetylated amino acid" as used herein refers to an amino acid having an acetyl moiety in its side chain.

As used herein, "pharmaceutically-acceptable" refers to those compounds, materials, compositions, and/or dosage forms that are, within the scope of sound medical judgment, suitable for contact with the tissues of human beings and animals without excessive toxicity, irritation, allergic response, or other problem complications commensurate with a reasonable benefit/risk ratio.

The term "pharmaceutically acceptable salt" refers to a derivative of the disclosed compounds wherein the parent compound is modified by making acid or base salts thereof, including acid addition salts and base addition salts. Examples of pharmaceutically-acceptable salts include, but are not limited to, mineral or organic acid salts of basic residues such as amines; alkali or organic salts of acidic residues such as carboxylic acids; and the like. The term "acid addition salt" refers to the corresponding salt derivative of a parent compound that has been prepared by the addition of an acid. The pharmaceutically-acceptable salts include the conventional salts or the quaternary ammonium salts of the parent compound formed, for example, from inorganic or organic acids. For example, such conventional salts include, but are not limited to, those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, adipic, alginic, aspartic, hydroxymaleic, phenylacetic, glutamic, benzoic, salicylic, sulfanilic, 2-acetoxybenzoic, fumaric, benzenesulfonic, toluenesulfonic, methanesulfonic, 2-napthalenesulfonic, ethane disulfonic, oxalic, isethionic, glucoheptanoic, glycerophosphoric, hemisulfanic, heptanoic, hexanoic, hydrochloric, hydrobromic, hydroiodic, 2-hydroxyethanesulfonic, 2-napthalenesulfonic, pectinic, phosphoric, sulfuric, 3-phenylpropionic, picric, pivalic, thiocyanic, p-toluenesulfonic, butyric, camphoric, camphorsulfonic, digluconic, cyclopentanepropionic, bisulfuric, dodecylsulfuric, ethanesulfonic, and undecanoic and the like. Thus, the term "base addition salt" refers to the corresponding salt derivative of a parent compound that has been prepared by the addition of a base. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. The pharmaceutically-acceptable salts include the conventional salts or the quaternary ammonium salts of the parent compound formed, for example, from inorganic or organic bases. For example, such conventional salts include, but are not limited to, those derived from inorganic bases such as lithium hydroxide, sodium hydroxide, potassium hydroxide, calcium hydroxide, magnesium hydroxide and ammonium hydroxide and the salts prepared from organic amines, such as methyl amine, ethyl amine, isopropyl amine, piperidine, piperizine, pyrrolidine, ethanolamine, morpholine, diazapine, ethylene diamine, pyridine, quinoline, quinuclidine, and the like.

The term "therapeutically effective amount," "effective amount" or "therapeutically effective dose" refers to that amount of the therapeutic agent sufficient to ameliorate a disorder, as described above. For example, for the given parameter, a therapeutically effective amount will show an increase or decrease of therapeutic effect at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control. In the context of the present invention, the effective amount of an adiponectin peptidomimetic compound can vary depending on co-administration of other therapeutics or disease profile of the individual (among other factors such as age, severity of disease, etc.).

The terms "therapy," "treatment," and "amelioration" refer to any reduction in the severity of symptoms. In the case of treating an ocular disorder, e.g., dry eye, the terms can refer to adding artificial tears, conserving tears, reducing tear evaporation, increasing tear production, reducing inflammation of the eyelids or eye surface, reducing ocular signs to dry eye, etc. As used herein, the terms "treat" and "prevent" are not intended to be absolute terms. Treatment can refer to any delay in onset, amelioration of symptoms, improvement in patient's quality of life, etc. The effect of treatment can be compared to an individual or pool of individuals not receiving the treatment, or to the same patient prior to treatment or at a different time during treatment. In some aspects, the severity of disease is reduced by at least 10%), as compared, e.g., to the individual before administration or to a control individual not undergoing treatment. In some aspects the severity of disease is reduced by at least 25%, 50%, 75%), 80%), or 90%, or in some cases, no longer detectable using standard diagnostic techniques.

The term "treating" or "treatment" refers to the treating or treatment of a disease or medical condition (such as dry eye or an ocular disease associated with inflammation) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating one or more symptoms of the disease or medical condition in a patient. The term encompasses the prophylactic treatment of a disease or condition as to prevent or reduce the risk of acquiring or developing a specific disease or condition, or to prevent or reduce the risk of recurrence.

As used herein, "dosage unit" refers to physically discrete units suited as unitary dosages for the particular patient to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "subject," "individual" or "patient" typically includes humans, but can also include other animals such as, e.g., other primates, rodents, canines, felines, equines, ovines, porcines, and the like.

III. Detailed Description of Embodiments

A. Adiponectin Peptidomimetic Compounds

Adiponectin is a 244 amino acid long polypeptide protein secreted mainly by the adipose tissue. This relatively large 30 kDa protein is structurally similar to tumor necrosis factor alpha (TNFα).

Adiponectin protein based biological modulators are still not available, partly due to difficulties in converting the full size adiponectin protein into a viable systemic regulator. The main reason of the non-drug ability of adiponectin protein is the extreme insolubility of the C-terminal domain and larger peptide fragments thereof. In addition, its relatively large size, and its propensity to form higher order complexes that alter its receptor binding affinities, poses significant challenges towards pharmaceutical manufacturing.

In one aspect of the invention, provided herein is an adiponectin peptidomimetic compound. In some embodiments, the compound is a compound represented by Formula I: X-$M_1$-SEQ ID NO: I-$M_2$-Z (I); wherein SEQ ID NO: 1 is Xaai-Ile-Pro-$Xaa_2$-Leu-Tyr-$Xaa_3$-Phe-Ala-$Xaa_4$-$Xaa_5$. In some embodiments, Xaai is Asn or a non-natural amino acid; $Xaa_2$ is Gly or a non-natural amino acid; $Xaa_3$ is Tyr or a non-natural amino acid; $Xaa_4$ is Tyr or a non-natural amino acid; and $Xaa_5$ is no amino acid, β-Ala or P-Ala-$NH_2$. In some instances, at least one of Xaai, $Xaa_2$, $Xaa_3$ or $Xaa_4$ is a non-natural amino acid. For instance, Xaai, $Xaa_2$, $Xaa_3$ or $Xaa_4$ is a non-natural amino acid. In some embodiments, Xaai and $Xaa_2$, Xaai and $Xaa_3$, Xaai and $Xaa_4$, $Xaa_2$ and $Xaa_3$, $Xaa_2$ and $Xaa_4$, and $Xaa_3$ and $Xaa_4$ are the same or different non-natural amino acids. In other embodiments, Xaai and $Xaa_2$ and $Xaa_3$, Xaai and $Xaa_2$ and $Xaa_4$, Xaai and $Xaa_3$ and $Xaa_4$, and $Xaa_2$ and $Xaa_3$ and $Xaa_4$ are the same or different non-natural amino acids. In yet other embodiments, Xaai and $Xaa_2$ and $Xaa_3$ and $Xaa_4$ are the same or different non-natural amino acids. In some embodiments, X is an optionally present 1-10 amino acid peptide (e.g., 1, 2, 3, 4, 5, 6, 7, 8, 9 or 10 amino acid peptide), polymer molecule, lipophilic compound or peptide transduction domain. In some embodiments, Z is an optionally present 1-10 amino acid peptide (e.g., 1, 2, 3, 4, 5, 6, 7, 8, 9 or 10 amino acid peptide), polymer molecule, lipophilic compound or peptide transduction domain. In some embodiments, $M_1$ is an optionally present single bond or a linking group. In some embodiments, $M_2$ is an optionally present single bond or a linking group. In some instances, the compound of Formula I comprising a C-terminal amino acid, and the C-terminal amino acid can be optionally amidated. In some embodiments, any of the compounds represented by Formula I are pharmaceutically acceptable salts thereof.

In some embodiments, Xaai is D-Asn and $Xaa_4$ is D-Ser. In some embodiments, $Xaa_2$ is Nva. In some embodiments, $Xaa_3$ is D-Ser. In some embodiments, $Xaa_2$ is Nva and $Xaa_3$ is D-Ser. In some embodiments, Xaai is D-Asn; $Xaa_2$ is Nva; $Xaa_3$ is D-Ser and $Xaa_4$ is D-Ser.

In some embodiments, X and/or Z is a 1-10 amino acid peptide, e.g., 1 amino acid peptide, 2 amino acid peptide, 3 amino acid peptide, 4 amino acid peptide, 5 amino acid peptide, 6 amino acid peptide, 7 amino acid peptide, 8 amino acid peptide, 9 amino acid peptide, or 10 amino acid peptide. In some instances, the length of the peptides and identity of the substituent amino acids comprising the X and Z peptides, are independently selected.

In some embodiments, $Xaa_5$ is β-Ala or P-Ala-$NH_2$. In some aspects, the compound of Formula I is selected from the group consisting of ADP355, ADP355-PAIa, ADP355-pAla-$NH_2$, ADP355-$NH_2$, ADP399, variants thereof, derivatives thereof; and pharmaceutically acceptable salts thereof. Detailed descriptions of ADP355, ADP399, and other useful adiponectin peptidomimetics are found, for example, in U.S. Pat. No. 9,073,965 and Otvos et al, Frontiers in Chemistry, 2014, 2(93): 1-15, doi: 10.3386/fchem.2014.00093, the disclosure is hereby incorporated by reference in its entirety for all purposes.

In some embodiments, X or Z is a polymer molecule, a lipophilic compound or an peptide transduction domain. In some embodiments, the polymer is a linear or branched polyethylene glycol. In other embodiments, the polymer has a molecular weight of from 1 kDa to 200 kDa, such as 1 kDa to 200 kDa, 50 kDa to 200 kDa, 100 kDa to 200 kDa, 1 kDa to 100 kDa, 1 kDa to 50 kDa, 50 kDa to 100 kDa, 1 kDa, 50 kDa. 100 kDa, 150 kDa or 200 kDa. In yet other embodiments, the polymer has a molecular weight of from 2 kDa to 95 kDa, such as 2 kDa to 95 kDa, 10 kDa to 95 kDa, 20 kDa to 95 kDa, 30 kDa to 95 kDa, 40 kDa to 95 kDa, 50 kDa to 95 kDa, 60 kDa to 95 kDa, 70 kDa to 95 kDa, 80 kDa to 95 kDa, 2 kDa to 90 kDa, 2 kDa to 80 kDa, 2 kDa to 70 kDa, 2 kDa to 60 kDa, 2 kDa to 50 kDa, 2 kDa to 40 kDa, 2 kDa to 30 kDa, 2 kDa to 20 kDa, 2 kDa to 15 kDa, 2 kDa to 10 kDa, 2 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, or 90 kDa. In some embodiments, the polymer has a molecular weight of from 5 kDa to 80 kDa, such as 5 kDa to 80 kDa, 5 kDa to 70 kDa, 5 kDa to 60 kDa, 5 kDa to 50 kDa, 5 kDa to 40 kDa, 5 kDa to 30 kDa, 5 kDa to 20 kDa, 5 kDa to 10 kDa, 70 kDa to 80 kDa, 60 kDa to 80 kDa, 50 kDa to 80 kDa, 40 kDa to 80 kDa, 30 kDa to 80 kDa, 20 kDa to 80 kDa, or 10 kDa to 80 kDa, 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, or 80 kDa. In other embodiments, the polymer has a molecular weight of from 12 kDa to 60 kDa, such as 12 kDa to 40 kDa, 20 kDa to 40 kDa, 12 kDa, 20 kDa, 30 kDa, 40 kDa, 50 kDa or 60 kDa. The X and Z polymer molecules are independently selected and may be the same or different.

In some embodiments, the polymer molecule is methoxyl PEG maleimide (mPEG(MAL)), methoxyl PEG forked maleimide (mPEG$_2$(MAL)), methoxyl PEG ortho-pyridyldisulfide (mPEG-OPSS), PEG-vinyl sulphone, or ortho-pyridyldisulfide-PEG-hydrazide (OPSS-PEG-hydrazide) in combination with methoxyl PEG aldehyde (mPEG-ALD). In other embodiments, the polymer molecule is selected from the group consisting of 5k-mPEG(MAL), 20k-mPEG (MAL), 40k-mPEG$_2$(MAL), 5k-mPEG-OPSS, IOk-mPEG-mPSS, 20k-mPEG-OPSS, or OPSS-PEG$_2$k-hydrazide in combination with mPEG$_{30}$ kD-ALD.

One of skill in the art will appreciate that when X is not present, M$_1$ will not be present either. One of skill in the art will appreciate that when Z is not present, M$_2$ will not be present either. One of skill in the art will appreciate that if the compound of Formula I has a C-terminus which comprises an amino acid, for example wherein the C-terminus comprises Z (if present and comprises a peptide or a transduction domain), Xaa$_5$ (if present) or Xaa$_4$, that amino acid is optionally amidated. One of skill in the art will appreciate that a peptide (for example a dipeptide having two amino acids Xaai and Xaa$_2$) can be represented as: H-Xaai-Xaa$_2$-OH, wherein H is part of the free amino terminus of the peptide and OH is part of the free carboxyl terminus of the peptide; or the peptide can be represented as: Xaai-Xaa$_2$, wherein the H is part of the free amino terminus of the peptide and the OH that is part of the free carboxyl terminus of the peptide are not shown in the formula for the peptide, but are understood to be present.

In other embodiments, the adiponectin peptidomimetic compound is a compound represented by Formula II: Xaai-Ile-Pro-Xaa2-Leu-Tyr-Xaa3-Phe-Ala-Xaa4-Xaa5 (SEQ ID NO:2) (II); wherein the C-terminal amino acid is optionally amidated; or a pharmaceutically acceptable salt thereof. In some embodiments, the adiponectin peptidomimetic compound selected from the group consisting of D-Asn-Ile-Pro-Nva-Leu-Tyr-D-Ser-Phe-Ala-D-Ser (SEQ ID NO:3), D-Asn-Ile-Pro-Nva-Leu-Tyr-D-Ser-Phe-Ala-D-Ser-p-Ala (SEQ ID NO:4), D-Asn-Ile-Pro-Nva-Leu-Tyr-D-Ser-Phe-Ala-D-Ser-p-Ala-H$_2$ (SEQ ID NO:5), D-Asn-Ile-Pro-Nva-Leu-Tyr-D-Ser-Phe-Ala-D-Ser-NH$_2$ (SEQ ID NO:6), (D-Asn-Ile-Pro-Nva-Leu-Tyr-D-Ser-Phe-Ala-D-Ser-His-Pro)$_2$-Dab-NH$_2$ (SEQ ID NO:7, wherein Dab represents 2,3-diamino butyric acid), a variant thereof, a derivative thereof, and a pharmaceutically acceptable salt thereof.

Useful adiponectin peptidomimetic compounds are described in U.S. Pat. No. 9,073,965, and Otvos et al., Frontiers in Chemistry, 2014, 2(93): 1-15, doi: 10.3389/fchem.2014.00093, the contents are hereby incorporated by reference in their entirety for all purposes.

One or more of the adiponectin peptidomimetic compound described herein can be included in a therapeutically effective composition such as an ophthalmic composition. In some embodiments, 1, 2, 3, 4, 5, 6, 7, 8, 9, 10 or more different adiponectin peptidomimetic compound can be contained in the composition. The amounts of each adiponectin peptidomimetic compound can be the same (or equal) or different. The activity of each adiponectin peptidomimetic compound can be the same or different.

1. Linking Groups (M$_1$ and M$_2$)

The linking group (M$_1$ or M$_2$) for coupling X or Z in a compound of Formula I may be any moiety that is at least bifunctional, provided that the resulting link between X or Z and the N-terminal or C-terminal amino acid or non-natural amino acid is stable. Suitable linking groups include bi- and multi-functional alkyl, aryl, aralkyl or peptidic moieties, alkyl, aryl or aralkyl aldehydes acids esters and anhydrides, sulfhydryl or carboxyl groups, such as maleimido benzoic acid derivatives, maleimido propionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups.

Optionally the linker group is selected so as to be sufficiently labile (e.g., to enzymatic cleavage by an enzyme present in the targeted tissue) so that it is cleaved following transport of a peptide of the invention, thereby releasing the peptide. Exemplary labile linkages are described in Low et al., U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

If the link formed by the linking group M$_1$ is between the Xaai and a carboxyl group of X (for example if X is a tagging element, the terminal carboxyl group of a peptidic tagging element or the terminal carboxyl group of a molecule), any amino acid (including, but not restricted to, .alpha.-amino acids including, but not restricted to, the proteinogenic amino acids) or peptide chain may form the link between Xaai and X.

In some embodiments, if the bonds between the M$_1$ or M$_2$ group and the peptides are amide bonds, the link may be formed by means of any functional groups capable of forming bonds between the Xaai or Xaa$_5$ and a —C(=O)- group of the terminal (or other) carboxyl group (or the terminal, or other —NH— group, or any other functional group of X or Z respectively). In other embodiments, if the link formed by the linking group M$_1$ is between the Xaai and an amino or carboxyl group of X, any amino acid or peptide chain may form the link between Xaai and X. In other embodiments, if the link formed by the linking group M2 is between the Xaa$_5$ and an amino or carboxyl group of Z, any amino acid or peptide chain may form the link between Xaa$_5$ and Z. Examples of suitable linking groups MI and M2 for connecting, for instance, the Xaai and a carboxyl group of X, the Xaai and an amino group of X, the Xaa$_5$ and a carboxyl group of Z, and the Xaa$_5$ and an amino group of Z, are described in U.S. Pat. App. Publication No. 2014/0057833, the disclosure of which is hereby incorporated in its entirety for all purposes.

2. Peptide Transduction Domain

In some embodiments, X and/or Z may comprise a protein transduction domain. A protein transduction domain includes a peptide that is capable of crossing cell membranes and of directing the transport of a peptide, protein, or molecule associated with the protein transduction domain; from the outside of a cell into the cytoplasm of the cell through the cytoplasmic membrane of the cell. In some instances, the protein transduction domain comprises a relatively short sequence derived from a naturally occurring protein, such as the TAT protein of HIV, the antennapedia protein from Drosophila, and the VP22 protein from the herpes simplex virus. Non-limiting examples of suitable protein transduction domains are described in, e.g., Handbook of Cell-Penetrating Peptides, by Ulo Langel (Editor) (CRC Press, 2nd Edition, 2006). Cell-Penetrating Peptides: Process and Applications, by Ulo Langel (Editor) (CRC Press, I .sup.st Edition, 2002); E. L. Snyder, et al, Pharm. Res., 2004, 21(3), 389-93. Beerens et al., Current Gene Therapy, 2003, 3(5), 486-94; Hudec et al., Med. Res. Rev., 2005, 25(6), 679-736. Detailed descriptions of useful protein transduction domains are found in, e.g., U.S. Pat. App. Publication No. 2014/0057833, the disclosure of which is hereby incorporated in its entirety for all purposes.

3. Preparing Adiponectin Peptidomimetic Compounds

Peptidomimetic compounds of the present invention may be natural peptides, recombinant peptides or synthetic peptides. They may also be chemically synthesized, using, for example, solid phase synthesis methods. Additionally, peptide transduction domains appended to peptides of the invention may be natural or synthetic peptides, and may be either prepared by isolation from natural sources or may be synthesized.

The peptides of the present invention may be synthesized de novo using peptide synthesis methods. In such methods. the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroacetic acid (TFA), HCl in dioxane, boron tris-(trifluoracetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In some embodiments, the peptide synthesis method may follow Merrifield solid-phase procedures. See, e.g., Merrifield, J. Am. Chem. Soc, 1963. 85, 2149-54. Additional information about the solid phase synthetic procedure can be obtained from, for example, Solid Phase Peptide Synthesis: A Practical Approach by E. Atherton and R. C. Sheppard (Oxford University Press. 1989, Solid phase peptide synthesis, by J. M. Stewart and J. D. Young, (2nd edition, Pierce Chemical Company. Rockford, 1984), and the review chapters by R. Merrifield in Advances in Enzymology 32:221-296, edited by F. F. Nold (Interscience Publishers, New York, 1969) and by B. W. Erickson and R. Merrifield in The Proteins Vol. 2, pp. 255 et seq., edited by Neurath and Hill, (Academic Press, New York, 1976). Peptide synthesis may follow synthetic techniques such as those set forth in Fields et al., Introduction to Peptide Synthesis, in Current Protocols in Molecular Biology (Chapter 11, Unit 11.15; John Wiley and Sons, 2008) and Amblard et al. (2006, Molecular Biotechnology, 33:239-254).

The synthesis of peptides by solution methods is described in, for example, The Proteins, Vol. 11, edited by Neurath et al. (3rd Edition, Academic Press 1976). Other general references to the synthesis of peptides include: Peptide Synthesis Protocols, edited by M. W. Pennington and Ben M. Dunn (Humana Press 1994), Principles of Peptide Synthesis, by Miklos Bodanszky (2nd edition, Springer-Verlag, 1993), and Chemical Approaches to the Synthesis of Peptides and Proteins by Paul Lloyd-Williams, F. Albericio, E. Giralt (CRC Press 1997), and Synthetic Peptides: A User's Guide, edited by G. Grant (Oxford University Press, 2002).

Alternatively, peptides may be prepared utilizing recombinant DNA technology, which comprises combining a nucleic acid encoding peptides of Formula I or II in a suitable vector, inserting the resulting vector into a suitable host cell, recovering the peptide subsequently produced by the host cell, and purifying the polypeptide recovered. The required techniques of recombinant DNA and protein technology are known to the ordinary skilled artisan. General methods for the cloning and expression of recombinant molecules are described in Molecular Cloning by Sambrook et al. (Cold Spring Harbor Laboratories, Second Ed., 1989) and in Current Protocols in Molecular Biology by Ausubel (Wiley and Sons, 1987).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

The compounds of the invention, whether prepared by chemical synthesis or recombinant DNA technology, may be purified using known techniques, for example preparative HPLC, FPLC, affinity chromatography, as well as other chromatographic methods. Isolated compounds may then be assessed for biological activity according to the methods described herein, as well as by any methods known to the skilled artisan.

For synthetic techniques, peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent.

The amino acid Xaai, $Xaa_5$ or $Xaa_4$ when $Xaa_5$ is zero amino acid may be conjugated to a lipophilic compound comprising X or Z either directly or by use of a linker. The lipophilic compound may be a natural compound such as a saturated or unsaturated fatty acid, a fatty acid diketone, a terpene, a prostaglandin, a vitamin; a carotenoid or steroid or a synthetic compound such as a carbon acid, an alcohol, an amine and sulphonic acid with one or more alkyl-, aryl-, alkenyl-, or other multiple unsaturated compounds. The conjugation between the amino acid and the lipophilic compound, optionally through a linker may be done according to methods known in the art, e.g. as described by Bodanszky in Peptide Synthesis. John Wiley. New York, 1976 and in WO 96/12505.

To covalently attach a polymer molecule to an amino acid of the compound described herein, the hydroxyl end groups of the polymer molecule must be provided in activated form, i.e., with reactive functional groups (for example primary amino groups, hydrazide (HZ), thiol, succinate (SUC), succinimidyl succinate (SS), succinimidyl succinamide (SSA), succinimidyl proprionate (SPA), succinimidyl carboxy methyl ate (SCM), benzotriazole carbonate (BTC), N-hydroxysuccinimide (NHS), aldehyde, nitrophenyl carbonate (NPC), and tresylate (TRES). Specific examples of activated PEG polymers include the following linear PEGs: NETS-PEG (e.g. SPA-PEG, succinimidyl succinate proprionate-PEG (S SPA-PEG), SBA-PEG, SS-PEG, SSA-PEG, succinimidyl carbonate-PEG (SC-PEG), succinimidyl glutarate-PEG (SG-PEG), and SCM-PEG and NOR-PEG), BTC-PEG, epoxide-PEG (EPDX-PEG), isocyanate-PEG (NCO-PEG), NPC-PEG, carbonylimidazole-PEG (CDI-PEG), aldehyde-PEG (ALD-PEG), TRES-PEG, VS-PEG, iodo-PEG, and maleimide-PEG (MAL-PEG), and branched PEGs such as PEG2-NHS and those disclosed in U.S. Pat. Nos. 5,932,462 and 5,643,575, both of which references are hereby incorporated by reference in their entirety. The PEGylation may be directed towards specific attachment groups, e.g., the N-terminal amino group (U.S. Pat. No. 5,985,265). Furthermore, the conjugation may be achieved in one step or in a stepwise manner (e.g. as described in WO 99/55377).

B. Ocular Disorders Amenable to Treatment with Adiponectin Peptidomimetic Compounds The adiponectin peptidomimetic compounds described herein can be used to treat an ocular disease or disorder, including dry eye or an ocular disease associated with inflammation.

Dry eye disease or keratoconjunctivitis sicca (KCS) can be caused by or associated with various conditions including, but not limited to Sjogren syndrome, ocular cicatricial pemphigoid, congenital alacrima, blepharitis, lacrimal gland ablation, age-related lacrimal gland deficiency, alacrima (e.g., Triple A or Allgrove syndrome, and Riley-Day syndrome), lacrimal gland infiltration (e.g., sarcoidosis, lymphoma, and AIDS), lacrimal gland duct obstruction, meibomian gland disorder, pterygium, chronic inflammation of the conjunctiva, reflex block, herpes zoster, ocular allergies, autoimmune disease, chronic graft-versus-host disease, the natural aging process, diabetes, long-term contact lens wear, dry environment, excessive computer screen use, surgery that involves corneal incisions or ablates corneal nerves (e.g., cataract surgery, refractive surgery, retinal surgery, ocular tumor therapy, medications, decreased blinking (low blink rate), disorders of lid aperature or lid/globe dynamics, pregnancy, polycystic ovary syndrome, acne rosacea, lupus, scleraderma, sarcoidosis, Stevens-Johnson syndrome, Parkinson's disease, thyroid disease, cosmetic surgery, smoking, radiation therapy, vitamin A deficiency, and menopause.

Dry eye can also be caused by nutritional disorders and deficiencies, pharmacologic side effects, skin disease on and around the eyelids, eye stress and glandular and tissue destruction, environmental exposure to smog, smoke, excessively dry air, airborne particulates, autoimmune and other immunodeficient disorders. In dry eye, the ocular surface epithelium undergoes squamous metaplasia, manifested by loss of goblet cells, mucin deficiency and keratinization. These changes result in tear film instability, which leads to the clinical symptoms of dry eye syndrome.

Symptoms of dry eye include stinging, burning or scratchy sensation in the eye; ocular dryness or grittiness; stringy mucus in or around the eye; increase eye irritation; eye fatigue; sensitivity to light (photophobia); eye redness; excessive tearing; episode of blurred vision; foreign body sensation in the eye; pain or soreness around or in the eye; inability to cry when emotionally stressed; decreased tolerance of an activity requiring sustained visual attention; and any combination thereof. Symptoms of dry eye can be quantified using, for example, in the Ocular Surface Disease Index (OSDI) questionnaire, which lists 12 symptoms and grades each on a scale of 1-4. Clinical signs of dry eye can be assessed, for example, by performing impression cytology (e.g., ocular surface staining), measuring tear breakup time (TBUT), performing the Schirmer's test, performing a phenol red thread tear test, and measuring the components of tears (e.g., analysis of tear proteins or tear-film osmolarity). Elevated osmolarity (hyperosmolarity) may cause less regulation of tear film, more damage to the ocular surface, and in some cases, increased inflammation of the eye.

Ocular diseases associated with inflammation include, but are not limited to, uveitis, dry eye, keratitis, allergic eye disease, infectious keratitis, herpetic keratitis, corneal angiogenesis, lymphangiogenesis, uveitis, pterygium, retinitis, choroiditis, acute multifocal placoid pigment epitheliopathy, Behcet's disease, post-surgical corneal wound healing, conditions caused by laser, conditions caused by photodynamic therapy, wet and dry age-related macular degeneration (ARMD), conditions affecting the posterior part of the eye, maculopathies, retinal degeneration, non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi and Harada syndrome, retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease, sympathetic ophthalmia, uveitic retinal disease, retinal detachment, trauma, conditions caused by photodynamic therapy, photocoagulation, hypoperfusion during surgery, radiation retinopathy, and bone marrow transplant retinopathy, proliferative vitreal retinopathy and epiretinal membranes, proliferative diabetic retinopathy, ocular histoplasmosis, ocular toxocariasis, presumed ocular histoplasmosis syndrome (PONS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, myiasis, retinitis pigmentosa, systemic disorders with accosiated retinal dystrophies, congenital stationary night blindness, cone dystrophies, Stargardt's disease, fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum; retinal detachment, macular hole, giant retinal tear, retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors, other diseases affecting the posterior part of the eye, punctate inner choroidopathy, acute posterior multifocal placoid pigment epitheliopathy, myopic retinal degeneration, acute retinal pigment epitheliitis, postsurgical corneal inflammation, corneal transplantation, blepharitis, MGD, glaucoma, ocular hypertension, branch vein occlusion, retinal diseases, Best's vitelliform macular degeneration, retinitis pigmentosa, proliferative vitreoretinopathy (PVR), and any other degenerative diseases of either the photoreceptors or the retinal pigment epithelial (RPE).

Symptoms or clinical signs of ocular diseases associated with inflammation include, but are not limited to, unstable tear film, chronic hyperosmolar stress, evaporative tear loss, decreased lubricity, other tear deficiencies that lead to an increased in pro-inflammatory response in the eye, inflammation, and any combination thereof.

C. Pharmaceutical Compositions

The adiponectin peptidomimetic compounds can be used and formulated into any of a number of pharmaceutical compositions, including those described in the United States Pharmacopeia (U.S.P.), Goodman and Gilman's The Pharmacological Basis of Therapeutics, IO.sup.th Ed., McGraw Hill, 2001; Katzung, Ed., Basic and Clinical Pharmacology, McGraw-Hill/Appleton & Lange, 8th ed., Sep. 21, 2000; Physician's Desk Reference (Thomson Publishing; and/or The Merck Manual of Diagnosis and Therapy, 18th ed., 2006, Beers and Berkow, Eds., Merck Publishing Group; or, in the case of animals, The Merck Veterinary Manual, 9th ed., Kahn Ed., Merck Publishing Group, 2005.

Ophthalmic pharmaceutical compositions may also contain one or more excipients or other substances, such as preservatives, antioxidants, pH adjusting agents, buffering agents, gelling agents, viscosity enhancers, surfactants, solubility agents, lubricating agents, salts, co-solvents, diluents, carriers, adjuvants, oils, humectants, emollients, stabilizers, emulsifying agents, and/or dispersing agents. Other agents may be employed in the compositions for a variety of purposes. By way of example, injectable compositions may contain various excipients or other substances, such as preservatives, antioxidants, pH adjusting agents, buffering agents, salts, emulsifying agents, and/or dispersing agents. Non-limiting examples of a preservative such as a water-soluble preservative include sodium bisulfite, sodium bisulfate, sodium thiosulfate, benzalkonium chloride, chlorobutanol, thimerosal, ethyl alcohol, methylparaben, polyvinyl alcohol, benzyl alcohol, and phenylethyl alcohol. Examples of ophthalmically acceptable antioxidants include, but are not limited to, sodium bisultite, sodium thiosulfate, acetyl cysteine, cysteine, thioglycerol, sodium sulfite, acetone sodium bisulfite, dithioerythreitol, dithiothreitol, thiourea, and erythorbic acid. Useful examples of ophthalmically acceptable pH adjusting agents, such as an acid, base and/or buffer include but are not limited to, an acid such as acetic, boric, citric, lactic, phosphoric, sulfuric, and hydrochloric acids; a base such as sodium hydroxide, sodium phosphate, sodium borate, sodium citrate, sodium acetate, sodium lactate and tris-hydroxymethylarainomethane, triethanolamine; and/or a buffer such as citrate/dextrose, sodium bicarbonate and ammonium chloride or an amino acid. Such an acid, base and/or buffer can be included in an amount sufficient to adjust pH of the composition to an ophthalmically acceptable range.

The composition can be formulated for topical ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. The ophthalmic vehicles include, but are not limited to, saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Alternatively, the compounds can be formulated for injection into the eye, such as intravitreal injection subj conjunctival injection and injection into the anterior chamber of the eye. In other instances, the compounds may be in a form suitable for implantation use, e.g., as entrapped in microcapsules. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). The compositions can be also in an ophthalmic depot formulation, such as for subconjunctival administration. The adiponectin peptidomimetics can be embedded in in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all the active agent. The depot formulation can be a liquid formulation, comprising a pharmaceutical acceptable polymer and a dissolved or dispersed active agent, upon injection, the polymer forms a depot at the injections site, e.g., by gelifying or precipitating. The composition can comprise a solid article that can be inserted in a suitable location in the eye, such as between the eye and eyelid or in the conjuctival sac, where the article releases the active agent. Solid articles suitable for implantation in the eye in such fashion generally comprise polymers and can be bioerodible or non-bioerodible.

Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for ocular use. The therapeutically efficient amount typically is between about 0.0001% (wt) and about 90% (wt), preferably about 0.0001% (wt) to about 50% (wt) in liquid formulations.

Alternatively, the active compounds may be applied to the eye via liposomes. Further, the active compounds may be infused into the tear film via a pump-catheter system. In some embodiments, the active compound is contained within a continuous or selective-release device, for example, membranes such as, but not limited to, those employed in the pilocarpine (Ocusert™) System (Alza Corp., Palo Alto, Calif). In some embodiments, the active compounds is contained within, carried by, or attached to contact lenses which are placed on the eye. In other embodiments, the active compound is contained within a swab or sponge which can be applied to the ocular surface. In another embodiment, the active compound is contained within a liquid spray which can be applied to the ocular surface. In another embodiment, the active compound is injected directly into the lacrimal tissues or onto the eye surface.

When the pharmaceutical composition for treating dry eye is used as an ophthalmic solution, it is provided in any dosage form which is used for ophthalmic solution, for example, an aqueous eye drop such as aqueous ophthalmic solution, aqueous suspended ophthalmic solution, viscous ophthalmic solution and solubilized ophthalmic solution, or a non-aqueous ophthalmic solution such as non-aqueous ophthalmic solution and non-aqueous suspended ophthalmic solution. Among these, the aqueous ophthalmic solution is preferable.

When the pharmaceutical composition for treating dry eye is prepared into an aqueous ophthalmic solution, various additives normally used in the aqueous ophthalmic solution are conveniently contained therein as long as the object of the present invention is not adversely affected. Examples of such the additives include buffers, isotonizing agents, preservatives, solubilizers (stabilizers), pH adjusting agents, osmolarity adjusting agents, thickeners and chelating agents.

The buffers may be selected from, but not limited to, the group comprising a phosphate buffer, a borate buffer, a citrate buffer, a tartrate buffer, an acetate buffer (for example, sodium acetate) and an amino acid. The isotonizing agents may be selected from, but not limited to, the group comprising sugars such as sorbitol, glucose and mannitol, polyhydric alcohols such as glycerin, polyethylene glycol and polypropylene glycol, and salts such as sodium chloride. The preservatives may be selected from, but not limited to, the group comprising benzalkonium chloride, benzethonium chloride, alkyl paraoxybenzoates such as methyl paraoxybenzoate and ethyl paraoxybenzoate, benzyl alcohol, phenethyl alcohol, sorbic acid and salts thereof, thimerosal and chlorobutanol. The solubilizers (stabilizers) may be selected from, but not limited to, the group comprising cyclodextrin and derivatives thereof, water-soluble polymers such as polyvinylpyrrolidone), and surfactants such as polysorbate 80 (trade name: Tween 80). The pH adjusting agents may be selected from, but not limited to, the group comprising hydrochloric acid, acetic acid, phosphoric acid, sodium hydroxide, potassium hydroxide and ammonium hydroxide. The thickeners may be selected from, but not limited to, the group comprising hydroxyethylcellulose, hydroxypropylcellulose, methylcellulose, hydroxypropylmethylcellulose and carboxymethylcellulose and salts thereof. The chelating agents may be selected from, but not limited to, the group comprising sodium edetate, sodium citrate and sodium condensed phosphate.

For ophthalmic application, preferably solutions are prepared using a physiological saline solution as a major vehicle. The pH of such ophthalmic solutions should preferably be maintained between 4.5 and 8.0; about 5 to 7.5; preferably 6 to 7 with an appropriate buffer system, a neutral pH being preferred but not essential. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (tris-hydroxymethylamino-methane), and the like. Salts and buffers include citrate/dextrose, sodium bicarbonate, ammonium chloride and mixtures of the aforementioned acids and bases.

The osmotic pressure of the aqueous ophthalmic composition is generally from about 200 to about 400 milliosmolar (mOsM), more preferably from 260 to 340 mOsM. The osmotic pressure can be adjusted by using appropriate amounts of physiologically and ophthamologically acceptable ionic or non-ionic agents. Sodium chloride is a preferred ionic agent, and the amount of sodium chloride ranges from about 0.01% to about 1% (w/v), and preferably from about 0.05% to about 0.45% (w/v). Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can be used in addition to or instead of sodium chloride to achieve osmolality within the above-stated range. Further, non-ionic agents such as mannitol, dextrose, sorbitol, glucose and the like can also be used to adjust the osmolality.

Tonicity adjusters may be added as needed or convenient. They include, but are not limited to, salts, particularly sodium chloride, potassium chloride, mannitol and glycerin, or any other suitable ophthalmically acceptable tonicity adjuster. Various buffers and means for adjusting pH may be used so long as the resulting preparation is ophthalmically acceptable. Accordingly, buffers include acetate buffers, citrate buffers, phosphate buffers and borate buffers. An ophthalmically acceptable antioxidant for use in the present invention includes, but is not limited to, sodium metabi sulfite, sodium thiosulfate, acetylcysteine, butylated hydroxyanisole and butylated hydroxytoluene.

When the pharmaceutical composition for treating dry eye is prepared into an ophthalmic ointment, a base compound must be present. The base of the ophthalmic ointment may be selected from but not limited by the group comprising purified lanolin, VASELINE® plastibase, liquid paraffin and polyethylene glycol.

The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Alternatively, the composition of the invention can be formulated for oral administration using pharmaceutically acceptable tableting excipients including lactose, microcrystalline cellulose, corn starch, stearic acid, or the like, can be used. Oral administration can also comprise a liquid composition formulated in water, glycols, oils, alcohols or the like.

The adiponectin peptidomimetic compounds can be formulated into lipid-based nanocarriers, such as solid lipid nanoparticles, nanostructured lipid carriers, lipid-drug conjugates, and coated-liposomes.

The formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five units doses, where a typical unit dose is from one to about 8 drops, preferably one to about 3 drops. The volume of one drop usually is about 20-35 µl.

The formulations may be in the form of a sterile solution or suspension. The solution or suspension can be for topical or injectable application. It can be in a sterile injectable formulation, e.g., a liquid or suspension formulation. In some embodiments, it may be formulated according to known methods using suitable dispersing or wetting agents and suspending agents. The sterile injectable preparation may also be a sterile injectable solution or suspension in a non-toxic intraocularly- or intravitreally-acceptable diluent or solvent. Buffers, preservatives, antioxidants, and the like can also be incorporated as required.

Provided herein are kits comprising the ophthalmic composition or formulation described herein. In some embodiments, the kit also includes instructions for administering the composition or formulation. In some cases, the composition or formulation is packaged in a form suitable for metered application. In other cases, the composition or formulation is packaged for single unit dose use.

D. Methods of Administration

The composition provided herein can be administered to the eye. In some embodiments, the composition is applied to the palpebral part of the eye, such as the external portion of the upper and lower eyelids and the medial and lateral canthus, and/or the ocular surface of the eye. In some instances, the compositions can be administered to an afflicted eye conjunctival sac. In some embodiments, the composition is administered topically, by intravitreal injection, by subconjunctival injection, by conjunctival injection, by intramuscular injection, by subcutaneous injection, by intravenous injection, by intracameral injection, or by implantation into the subject's eye. In some cases, administration includes intravitreal depot implantation or other ophthalmic drug delivery methods described in, e.g., Edelhauser et al., Invest Ophthalmol Vis Sci, 2010, 51(11):5403-5420. The eye includes, but is not limited to, a tissue, gland, vessel, lens, muscle, nerve, or other structure in or around the eye such as an ocular tissue, ocular surface, ocular chamber, eyelid, nasolacrimal duct, meibomian gland, and lacrimal gland.

The composition can be formulated for ophthalmic application, for example, in the form of solutions, ointments, creams, lotions, eye ointments and, most preferably, eye drops or eye gels and can contain the appropriate conventional additives, including, for example, preservatives, solvents to assist drug penetration, and emollients in ointments and creams. Such topical formulations can contain compatible conventional carriers, for example cream or ointment bases, and ethanol or oleyl alcohol for lotions.

The composition can be administered to the eyes of a patient by any suitable means, but are preferably administered as a liquid or gel suspension in the form of drops, spray or gel. In one embodiment, the formulation is in the form of drops, and is dropped onto the ocular surface. In another embodiment, the formulation is contained within a swab or sponge which can be applied to the ocular surface. In another embodiment, the formulation is contained within a liquid spray or ointment which can be applied to the ocular surface. In another embodiment, the formulation is injected directly into the eye, such as into the lacrimal tissues or onto the eye surface. In a further embodiment, the formulation is first applied on a fingertip or other applicator, then applied or rubbed directly onto the lid margin or canthus. Alternatively, the adiponectin peptidomimetic compound can be applied to the eye via a colloidal dosage form such as nanoparticular, nanomicelles, liposomes, and microemulsions. Further, the composition can be infused into the tear film via a pump-catheter system. Another embodiment involves the adiponectin peptidomimetic compound contained within a continuous or selective-release device, for example, membranes. As an additional embodiment, the adiponectin peptidomimetic compound can be contained within, carried by, or attached to contact lenses or other compatible controlled release materials, which are placed on the eye or around the eye.

In some embodiments, the compositions are administered topically, intraocularly, intracamerally, intraorbitally, periocularly, intravitreally, subconjunctivally, conjunctivally, intramuscularly, subcutaneously, intravenously, intracamerally, or via other routes in or around the eye. Non-limiting delivery routes for the therapeutic compositions described herein include aqueous solution, oily solutions, e.g., ointments, colloidal carriers, e.g., micelles, emulsions, liposomes, nanoparticles, solids forms, e.g., collagen-based shields and/or particles, and drug-loaded punctual plugs, drug-loaded canalicular plugs, contact lenses, implants and inserts.

The suitability of a particular route of administration will depend in part on the pharmaceutical composition, its components, the disorder being treated, and the subject in need of the therapy.

E. Dosing

The dosage of a therapeutic agent administered to a subject will vary depending on a wide range of factors. For example, it would be necessary to provide substantially larger doses to humans than to smaller animals. The dosage will depend upon the size, age, sex, weight, medical history and condition of the subject, and the nature of the dry eye disease being treated, use of other therapies, the potency of the substance being administered, and the frequency of administration. The skilled artisan will be able to determine appropriate dosages depending on these and other factors. For example, when the therapeutic agent can be used as an ophthalmic solution for treating dry eye in a subject in need thereof, it can be desirable that the aqueous solution eye drop contain the therapeutic agent in an amount of about 0.001% (wt) to 30% (wt), e.g, about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.6% (wt), about 0.7% (wt), about 0.8% (wt), about 0.9% (wt), about 1% (wt), about 2% (wt), about 3% (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19%

(wt), about 20% (wt), about 21% (wt), about 22% (wt), about 23% (wt), about 24% (wt), about 25% (wt), about 26% (wt), about 27% (wt), about 28% (wt), about 29% (wt), about or 30% (wt). In some embodiments, the therapeutic agent can be in an amount ranging from about 0.001% (wt) to about 30% (wt), about 0.005% (wt) to about 30% (wt), about 0.01% (wt) to about 30% (wt), about 0.1% (wt) to about 30% (wt), about 1% (wt) to about 30% (wt), about 10% (wt) to about 30% (wt), about 20% (wt) to about 30% (wt), about 10% (wt) to about 20% (wt), about 0.001% (wt) to about 10% (wt), about 0.001% (wt) to about 1% (wt), about 0.001% (wt) to about 0.1% (wt), 0.01% (wt) to about 0.1% (wt), and the like. When administered, the therapeutic agent can be given once daily or with multiple daily doses such as twice per day, three times per day and four times per day. In some embodiments, the therapeutic agent can be administered once a day, every other day, or less frequently. The therapeutic agent can be administered when the subject has one or more symptoms of dry eye or an ocular disease. In some instances, the therapeutic agent can be given in a dose of one to five drops or more, for example, one drop, two drops, three drops, four drops, five drops or more. When administered, the compositions may be given once daily or with multiple daily doses such as twice per day, three times per day four times per day, five times per day or more. In some embodiments, the therapeutic agent can be administered less frequently then once daily. For instance, the therapeutic agent can be administered every week, every 2 weeks, every 3 weeks, every 4 weeks, every 6 weeks, every 7 weeks, every 8 weeks, or less frequently. In some embodiments, the therapeutic agent can be administered according to the severity of the symptoms experienced by the subject.

Lifitegrast when administered topically, e.g., as eye drops or ointments, or for intraorbital or perio-ocular injection, exemplary dosages can be from about 0.1 mg/ml to about 200 mg/ml.

An effective amount of an adiponectin peptidomimetic compound will depend on the age, sex and weight of the patient, the current medical condition of the patient and the nature of the dry eye disease being treated. The skilled artisan will be able to determine appropriate dosages depending on these and other factors. For example, when the pharmaceutical composition is used as an ophthalmic solution for treating dry eye in a subject in need thereof, it is desirable that the aqueous solution eye drop contain the adiponectin peptidomimetic compound in an amount of about 0.0001% (wt) to 90% (wt), e.g., about 0.0001% (wt), about 0.0005% (wt),about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.6% (wt), about 0.7% (wt), about 0.8% (wt), about 0.9% (wt), about 1% (wt), about 2% (wt), about 3% (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19% (wt), about 20% (wt), about 21% (wt), about 22% (wt), about 23% (wt), about 24% (wt), about 25% (wt). about 26% (wt), about 27% (wt), about 28% (wt), about 29% (wt), about), about 30% (wt), about 31% (wt), about 33% (wt), about 33% (wt), about 34% (wt), about 35% (wt), about 36% (wt), about 37% (wt), about 38% (wt), about 39% (wt), about 40% (wt), about 41% (wt), about 42% (wt), about 43% (wt), about 44% (wt), about 45% (wt), about 46% (wt), about 47% (wt), about 48% (wt), about 49% (wt), about 50% (wt), about 51% (wt), about 52% (wt), about 53% (wt), about 54% (wt), about 55% (wt), about 56% (wt), about 57% (wt), about 58% (wt), about 59% (wt), about 60% (wt), about 61% (wt), about 62% (wt), about 63% (wt), about 64% (wt), about 66% (wt), about 66% (wt), about 67% (wt), about 68% (wt), about 69% (wt), about 70% (wt), about 71% (wt), about 72% (wt), about 73% (wt), about 74% (wt), about 75% (wt), about 76% (wt), about 77% (wt), about 78% (wt), about 79% (wt), about 80% (wt), about 81% (wt), about 82% (wt), about 83% (wt), about 84% (wt), about 85% (wt), about 86% (wt), about 87% (wt), about 88% (wt), about 89% (wt), about or 90% (wt). In some embodiments, the adiponectin peptidomimetic compound in an amount ranging from about 0.0001%) (wt) to about 90% (wt), e.g., about 0.0001% (wt) to about 90% (wt), about 0.001% (wt) to about 90% (wt), about 0.005% (wt) to about 90% (wt), about 0.01% (wt) to about 90% (wt), about 0.1% (wt) to about 90% (wt), about 1% (wt) to about 90% (wt), about 10% (wt) to about 90% (wt), about 20% (wt) to about 90% (wt), about 30% (wt) to about 90% (wt), about 40% (wt) to about 90% (wt), about 50% (wt) to about 90% (wt), about 60% (wt) to about 90% (wt), about 70% (wt) to about 90% (wt), about 80% (wt) to about 90% (wt), about 10% (wt) to about 50% (wt), about 10% (wt) to about 40% (wt), about 10% (wt) to about 30% (wt), about 10% (wt) to about 20% (wt), about 0.0001% (wt) to about 10% (wt), 0.0001% (wt) to about 1% (wt), 0.0001% (wt) to about 0.1% (wt), 0.0001% (wt) to about 0.01% (wt), 0.0001% (wt) to about 0.001% (wt), about 0.001% (wt) to about 10% (wt), about 0.001% (wt) to about 1% (wt), about 0.001% (wt) to about 0.1% (wt), 0.01% (wt) to about 0.1% (wt), 0.01%) (wt) to about 1% (wt), and the like. When administered, the compositions can be given once daily or with multiple daily doses such as twice per day, three times per day and four times per day. In some embodiments, the compositions are administered once a day, every other day, or less frequently. The compositions can be administered when the subject has one or more symptoms of dry eye or an ocular disease. In some instances, the compositions are given in a dose of one to five drops or more, for example, one drop, two drops, three drops, four drops, five drops or more.

When the pharmaceutical composition is used as an ocular ointment, it is desirable that the ocular ointment contain the adiponectin peptidomimetic compound in an amount of about 0.0001% (wt) to 90% (wt), e.g., about 0.0001% (wt), about 0.0005% (wt), about 0.001% (wt), about 0.005% (wt), about 0.01% (wt), about 0.02% (wt), about 0.03% (wt), about 0.04% (wt), about 0.05% (wt), about 0.06% (wt), about 0.07% (wt), about 0.08% (wt), about 0.09% (wt), about 0.1% (wt), about 0.2% (wt), about 0.3% (wt), about 0.4% (wt), about 0.5% (wt), about 0.6% (wt), about 0.7% (wt), about 0.8% (wt), about 0.9% (wt), about 1% (wt), about 2% (wt), about (wt), about 4% (wt), about 5% (wt), about 6% (wt), about 7% (wt), about 8% (wt), about 9% (wt), about 10% (wt), about 11% (wt), about 12% (wt), about 13% (wt), about 14% (wt), about 15% (wt), about 16% (wt), about 17% (wt), about 18% (wt), about 19% (wt), about 20% (wt), about 21% (wt), about 22% (wt), about 23% (wt), about 24% (wt), about 25% (wt), about 26% (wt), about 27% (wt), about 28% (wt), about 29% (wt), about), about 30% (wt), about 31% (wt), about 33% (wt), about 33% (wt), about 34% (wt), about 35% (wt), about 36% (wt), about 37% (wt), about 38% (wt), about 39% (wt), about 40% (wt), about 41% (wt), about 42% (wt), about 43% (wt), about 44% (wt), about 45% (wt), about 46% (wt), about 47% (wt), about 48% (wt), about 49% (wt), about 50%

(wt), about 51% (wt), about 52% (wt), about 53% (wt), about 54% (wt), about 55% (wt), about 56% (wt), about 57% (wt), about 58% (wt), about 59% (wt), about 60% (wt), about 61% (wt), about 62% (wt), about 63% (wt), about 64% (wt), about 66% (wt), about 66% (wt), about 67% (wt), about 68% (wt), about 69% (wt), about 70% (wt), about 71% (wt), about 72% (wt), about 73% (wt), about 74% (wt), about 75% (wt), about 76% (wt), about 77% (wt), about 78% (wt), about 79% (wt), about 80% (wt), about 81% (wt), about 82% (wt), about 83% (wt), about 84% (wt), about 85% (wt), about 86% (wt), about 87% (wt), about 88% (wt), about 89% (wt), about or 90% (wt). In some embodiments, the adiponectin peptidomimetic compound in an amount ranging from 0.0001% (wt) to about 90% (wt), e.g., about 0.0001% (wt) to about 90% (wt), about 0.001% (wt) to about 90% (wt), about 0.005% (wt) to about 90% (wt), about 0.01% (wt) to about 90% (wt), about 0. 1% (wt) to about 90% (wt), about 1% (wt) to about 90% (wt), about 10% (wt) to about 90% (wt), about 20% (wt) to about 90% (wt), about 30% (wt) to about 90% (wt), about 40% (wt) to about 90% (wt), about 50% (wt) to about 90% (wt), about 60% (wt) to about 90% (wt), about 70% (wt) to about 90% (wt), about 80% (wt) to about 90% (wt), about 10% (wt) to about 50% (wt), about 10% (wt) to about 40% (wt), about 10% (wt) to about 30% (wt), about 10% (wt) to about 20% (wt), about 0.0001% (wt) to about 10% (wt), 0.0001% (wt) to about 1% (wt), 0.0001% (wt) to about 0.1% (wt), 0.0001% (wt) to about 0.0% (wt), 0.0001% (wt) to about 0.001% (wt), about 0.001% (wt) to about 10% (wt), about 0.001% (wt) to about 1% (wt), about 0.001% (wt) to about 0.1% (wt), 0.01% (wt) to about 0.1%) (wt), 0.01% (wt) to about 1% (wt), and the like. When administered, the compositions may be given once daily or with multiple daily doses such as twice per day, three times per day four times per day, 5 times per day or more. In some embodiments, the compositions are administered less frequently then once daily. For instance, the compositions can be administered every week, every 2 weeks, every 3 weeks, every 4 weeks, every 6 weeks, every 7 weeks, every 8 weeks, or less frequently. In some embodiments, the compositions are administered according to the severity of the symptoms experienced by the subject.

For adiponectin peptidomimetics administered topically, e.g., as eye drops or ointments, or for intraorbital or perio-ocular injection, exemplary dosages are in the range from about 0.001 to about 100 mg, e.g., in the range from about 0.1 to about 10 mg, for instance, applied once a day, twice a day, or more frequently. For ADP 355 administered topically, e.g., as eye drops or ointments, or for intraorbital or perio-ocular injection, exemplary dosages can be from about 0.01 mg/ml to about 200 mg/ml.

Having indicated that there is variability in terms of dosing, it is believed that those skilled in the art can determine appropriate dosing by administering relatively small amounts and monitoring the patient for therapeutic effect. If necessary, incremental increases in the dose can be made until the desired results are obtained. Generally, treatment is initiated with smaller dosages which may be less than the optimum dose of the therapeutic agent. Thereafter, the dosage is increased by small increments until the optimum effect under circumstances is reached. The total daily dosage can be divided and administered in portions during the day if desired.

The pharmaceutical preparation can be packaged or prepared in unit dosage form. In such form, the preparation is subdivided into unit doses containing appropriate quantities of the active component, e.g., according to the dose of the therapeutic agent. The unit dosage form can be a packaged preparation, the package containing discrete quantities of preparation. The composition can, if desired, also contain other compatible therapeutic agents.

The invention provides methods of treating and/or ameliorating dry eye or an ocular disease associated with inflammation in a subject in need thereof. The course of treatment is best determined on an individual basis depending on the particular characteristics of the subject. The treatment can be administered to the subject on a daily, twice daily, thrice daily, every other day, bi-weekly, weekly, monthly or any applicable basis that is therapeutically effective. The treatment can be administered alone or in combination with at least one other therapeutic agent, e.g., targeting the same ocular disorder or a related symptom. The additional agent can be administered simultaneously with the adiponectin peptidomimetic compound, at a different time, or on an entirely different therapeutic schedule (e.g., the adiponectin peptidomimetic compound can be administered daily, while the additional agent is weekly).

F. Co-administration with a Therapeutic Agent

In some embodiments, the methods provided herein include coadministration of the adiponectin peptidomimetic compound with one or more additional therapeutic agents. The term "coadministration" refers to administration of a first amount of an adiponectin peptidomimetic compound or a pharmaceutically acceptable salt thereof and a second amount of at least one other therapeutic agent, e.g., another therapeutic agent for treating an ocular disease, or a therapeutic agent to address associated symptoms, e.g., inflammation. In some instances, the adiponectin peptidomimetic compound and the other therapeutic agent are administered simultaneously or essentially simultaneously. The adiponectin peptidomimetic compound and the other therapeutic agent may be in a single pharmaceutical composition, or in multiple pharmaceutical compositions. In other instances, the adiponectin peptidomimetic compound and the other therapeutic agent are administered sequentially. In a sequential dosing, the adiponectin peptidomimetic compound and the other therapeutic agent are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. The combined administration includes coadministration, using separate formulations or a single pharmaceutical formulation, and consecutive administration in either order, wherein preferably there is a time period while both (or all) active agents simultaneously exert their biological activities.

In some embodiments, the one or more additional therapeutic agents include, punctual plugs, topical steroids topical tetracyclines, topical nonsteroidal anti-inflammatory drugs (NSAIDS, such as topical diclofenac and topical ketorolac), IL-1 antagonists, other inflammatory pathway antagonists or inhibitors, angiostatic peptides, angiostatic steroids, modulators/inhibitors of VEGF or FGF, glucocorticosteroids, leukotriene modulators, anti-histamines, cytokine modulators/inhibitors, growth factor modulators/inhibitors, T-cell inhibitors, oral or topical pilocarpine, vitamin A, tretinoin (e.g, all trans-retinoic acid), doxycycline, cyclosporine A (e.g., RESTASIS® (Allergan), azithromycin, mucin stimulants (e.g., Diquafasol (Inspire Pharmaceuticals) 15-(S)-HETE (Alcon), rebamipide (Otsuka) and ecabet (ISTA)), hormonal agents and lacrimal gland stimulants (e.g., androgen tears (Allergan)) and a tear substitute (e.g., artificial tears). In some cases, the compositions described herein are administered in combination with progesterone, synthetic progestogens, medroxyprogesterone acetate, norethindrone, norethindrone acetate, megestrol acetate, 17-a-hydroxyprogesterone caproate, norgestrel, and derivatives thereof. Additional therapeutic agents include lifitegrast, EBI-005 (Eleven Biotherapeutics), anakinra (Amgen), MIM-D3 (Mimitogen Pharmaceuticals), rebamipide (Otsuka Pharmaceuticals), tofacitinib (Pfizer), dexamethasone phosphate (EyeGate Pharmaceuticals), RGN-259 (RegeneRx), KPI-121 (loteprednol etabonate; Kala Pharmaceuticals), bromfenac (ISTA Pharmaceuticals), diquafosol tetrasodium (Merck and Co., Inc.), hydroxychloroquine (Sanofi-Aventis), rebamipide (Acucela Inc.), CF101 (Can-Fite BioPharma), lifitegrast (Shire), EBI-005 (Eleven Biotherapeutics), cyclosporine (haporine-S; DH Bio Co., Ltd.), rimexolone (Alcon Research), ecabet sodium (Bausch & Lomb Incorporated), rituximab (DEC Pharmaceuticals), tocilizumab (Hoffman-La Roche Ltd.), skQl (Mitotech, SA), cis-UCA (Herantis Pharma PLC), LME636 (Alcon Research), AGN-223575 (Allergan), ISV-101 (InSite Vision), OTX-DP (Ocular Therapeutix, Inc.), rivoglitazone (Santen Pharmaceutical Co.), mapracorat (Bausch & Lomb Incorporated), resolvin (Resolvyx), tasocitinib/tofacitinib (Pfizer), RU-101 (R-Tech Ueno, Ltd.), DNase (Genentech, Inc.), voclosporin (Lux Biosciences), P-321 (Pari on Sciences), ACCS (Stemnion, Inc.), AGN-23241 1 (Allergan), and those described in, e.g. Ridder and Karsolia, Clinical Optometry, 2015, 2015(7):91-102.

Lifitegrast is a small-molecule that inhibits the integrin, lymphocyte function-associated antigen 1 (LFA-1), a cell surface protein found on leukocytes. Lifitegrast can bind to LFA-1 which blocks LFA-1 from interacting with its cognate ligand, intercellular adhesion molecule 1 (ICAM-1). This mechanism down-regulates inflammation mediated by T lymphocytes.

U.S. Pat. No. 8,815,795 pertains to adiponectin, a 247 amino acid sequence suggested for the prevention or treatiment of an eye disease. It is proposed that adiponectin can decrease inflammatory cytokines and has efficacy for prevention or therapeutic benefit for diseases of the eye such as dry eye (syndrome), eye complications from the use of contact lenses, alleviating ocular surface irregularities, decreasing inflammatory cytokines, and increasing conjunctival goblet cell density as well as providing a composition for eye cleaners or lubricants for contact lenses wearer.

The combination of an adiponectin peptidomimetic compound with another therapeutic agent can result in an enhanced efficacy in the treatment of ocular diseases. Administration of the active agents individually, consecutively, simultaneously, in combination or on an entirely different schedule as compared to the administration for either active agent individually can result in greater anti-inflammatory activity and improved clinical efficacy. Clinical studies in animal models indicated both improved efficacy and greater anti-inflammatory activity (data not shown). A synergistic effect can also be observed. The synergy can allow for reduced dosages of the active agents when administered either individually, consecutively, simultaneously, in combination or on an entirely different schedule as compared to the dosages for either active agent individually. The reduced dosage can help reduce any side effects that may appear. Accordingly, in combination therapy, the effective amount of the additional (second) therapeutic agent and the effective amount of the adiponectin peptidomimetic compound are together effective to reduce the symptoms/effects of an ocular disease.

One of skill in medicine can best determine the appropriate dose of the additional therapeutic agent by considering the state of the patient, the recommended dose, the severity of disease, and the efficacy of administering the combination of the adiponectin peptidomimetic compound with the therapeutic agent. Synergistic effects resulting from the administering the combination of the adiponectin peptidomimetic compound with the therapeutic agent can also result.

G. Methods of Determining Therapeutic Efficacy

A variety of methods can be performed evaluate a subject's treatment response to the compositions provided herein. In some instances, an assay, test or measurement can be made to determine whether methods described herein have alleviated at least one symptom or clinical sign of dry eye or an ocular disease associated with inflammation. Detailed descriptions of methods for measuring or evaluating symptoms or clinical signs of dry eye or an ocular disease provided herein are found in, for example, Pult et al., Eye (Lund), 2011, 25(4): 502-510, Bhatnagar et al., Int J Opthalmol, 2015, 8(1): 174-81, Messmer, Dtsch Arztebl Int, 2015, 112(5): 71-82.

Changes in tear secretion can be assessed by the Schirmer's test, phenol red thread tear rest (PRTT) and other methods of determining the rate and quantity of tear production. Changes in tear clearance can be assessed by fluorescein clearance test and fluorophotometry. Ocular surface damage and corneal epithelial defects can be evaluated vital dye staining, e.g., fluorescein, rose bengal, and lissamine green staining. Cytology of the ocular surface can be analyzed by impression cytology, brush cytology, flow cytometry, and confocal microscopy. Tear film stability can be looked at by analyzing tear break-up time, using the Tear film Stability Analysis System (TSAS). wavefront aberrometry, laser scanning microscopy, functional visual acuity, and tear film interferometry. Tear volume change can be assessed by tear meniscus measurement. Lipid layer changes to tear film can be assessed by tear film interferometry, meibometry, and meibography. Tear evaporation assessment can be made by evaporimeter, closed chamber, and ventilated chamber. Improvements in tear film chemical properties can be assessed by tear osmolarity, depression of freezing point, vapor pressure osmometry, and conductivity (Ocusense). Biochemical analysis of tear composition may include mucin and lipid analyses. Improvement in the ocular surface can be visualized by using dyes (such as fluorescein, lisamine green or rose bengal and observing less irregular morphology and staining of the corneal or conjunctival epithelium, compared to baseline.

The alleviation of at least one symptom or a clinical sign of an ocular disease, such as dry eye and an ocular disease associated with inflammation, can be determined by comparing the degree of the symptom or clinical sign after treatment to the degree of the same symptom or clinical sample prior to treatment. If the degree of the symptom or clinical sign has decreased after treatment, then an improvement or alleviation can be indicated.

IV. Examples

The following examples are offered to illustrate, but not to limit, the claimed invention.

Example 1

Adiponectin Ppeptidomimetic Compounds to Treat an Animal Model of Dry Eye

The purpose of this study is to use the scopolamine model of dry eye to study the efficacy of an adiponectin peptidomimetic compound described herein.

A. Treatment Protocol

Male Sprague-Dawley rats weighing between 300 g and 350 g are obtained from Charles River (Wilmington, Mass.). Animals are housed in animal quarters under constant room temperature (22±1° C.), light conditions (12-h light/12-h dark cycle), and humidity (40-60%). Animals are anaesthetized before the surgical experiment and clinical examination with isofluorane.

Dry eye is induced using scopolamine (Sigma-Aldrich, St. Louis, Mo.), which is continuously and systemically delivered to the animals via an osmotic pump (2ML4 Alzet®; CedarLane, Burlington, Ontario) filled with scopolamine and implanted subcutaneously in the mid dorsal area between the scapulae. The wound is closed with 2-3 wound clips. After the surgery and again the next day, the animals are subcutaneously injected with Carprofen (0.5 mg/100 g) a non-steroidal anti-inflammatory drug and potent, long-acting analgesic in rodents. Animals are anaesthetized before the surgical pump implantation and before all clinical endpoint testing in an Isofluorane 99.9% USP (Abraxis Bioscience, Richmond Hill, Ontario) chamber. Scopolamine is delivered at 12.5 mg/day and, for technical reasons, the data is evaluated at day 14.

The sterile solution of 0.175 g/mL of scopolamine hydrobromide (Sigma-Aldrich, St. Louis Mo.) is prepared in saline (0.9%) and filtered through a 0.22 um syringe-end filter (Millex-GC, Millipore Corp., Bedford, Mass.). A 2ML4 Alzet® pumps is filled with 2 mL of 0.175 g/mL scopolamine solution according to the manufacturer's instructions.

B. Clinical Endpoints for Dry Eye and Results

Corneal Staining: clinical signs of corneal dryness are evaluated by fluorescein impregnation of the cornea. A drop of a 1% fluorescein sodium (Sigma-Aldrich, St. Louis, Mo.) solution made up in sterile saline is instilled in the conjunctival sac of the anaesthetized animal. The cornea is thereafter observed under blue light using a Portable Slit Lamp ophthalmoscope with blue cobalt filter (Reichert Ophthalmic Instruments, Depew, N.Y.) three minutes after fluorescein instillation. For each animal, the punctate fluorescent-positive area of the ocular surface is recorded in a blinded fashion. The score of this test is graded from 0 to 4, where 0=no staining, 1=<25% surface staining, 2=25-50% surface staining, 3=50-75%) surface staining and 4=>75%>surface staining.

Schirmer's test: Tear production is measured with Zone-Quick standardized phenol-red threads (FCI Ophthalmics, Marshfield Hills, Mass.). Animals are lightly sedated with Isoflurane. The threads are inserted in the lateral lower canthus and left in place for thirty seconds. The length of the stained moistened portion of the thread is measured in millimeters, using the scale provided with the threads to an accuracy of 1 mm.

The mean and standard deviation (SD) is used to characterize the data for each study group. A one-way analysis of variance (ANOVA) is performed for body weight and the ophthalmic signs for treatment groups at every observation using Graph Pad Prism 4.0C (Graph Pad Software Inc., La Jolla, Calif). When stratified by examination day, when the treatment group is statistically significant (p<0.05, two-tail), pair wise comparisons are performed. For comparison to the untreated control (Group 1 or A), adjustment with Dunnett's test is used. No corrections are made for multiple comparisons. P values between groups is calculated and the difference between each of a pair of means (reported P values as >0.05, <0.05, <0.01 or 0.001) is reported.

Example 2

Adiponectin Peptidomimetic Compounds to Treat a Mouse Model of Dry Eye Using Scopolamine Combined with a Desiccating Environment Six- to eight-week-old female C57BL/6 mice are used in these experiments. Experimental dry eye (EDE) is induced by subcutaneous injection of 0.5 mg/0.2 mL scopolamine hydrobromide (Sigma-Aldrich, St. Louis, Mo.) four times a day (8 AM, 11 AM, 2 PM, and 5 PM) with exposure to an air draft and 30% ambient humidity, as previously described. During these experiments, the animals' behavior, food, and water intake are not restricted. The mice are randomly assigned to six groups according to topical treatment administered as follows: (1) untreated (UT) control mice that are not exposed to desiccating stress or treated topically; (2) EDE control mice that receive no eye drops; (3) EDE mice treated with balanced salt solution (BSS; Alcon, Fort Worth, Tex.), (4) EDE mice treated with 0.001%) adiponectin peptidomimetic; (5) EDE mice treated with 0.01% adiponectin peptidomimetic; and (6) EDE mice treated with 0.1% adiponectin peptidomimetic. All treatment groups receive 2 microliters eye drops four times a day. Tear volume and corneal smoothness are measured at 5 and 10 days after treatment. Ten days after treatment, the mice are euthanized, and multiplex immunobead assay, histology, immunohistochemistry, and flow cytometry were performed. Each group consists of five animals, and the experiments are performed on four independent sets of mice.

Tear volume is measured using phenol red-impregnated cotton threads (Zone-Quick; Oasis, Glendora, Calif.), as previously described. The threads are placed in the lateral canthus for 20 seconds. The distances of threads wet by tears are measured using the SMZ 1500 microscope (Nikon, Tokyo, Japan). A standard curve is derived to convert distance into volume.

Severity of corneal surface irregularity is graded via measurement of the distortion of a white ring from the fiberoptic ring illuminator of the stereoscopic zoom microscope (SMZ 1500; Nikon) by two masked observers. The corneal irregularity severity score is calculated using a 6-point scale (0-5) based on the number of distorted quarters in the reflected ring, as follows: 0, no distortion; 1, distortion in one quarter of the ring; 2, distortion in two quarters; 3, distortion in three quarters; 4, distortion in all four quadrants; 5, severe distortion, in which no ring could be recognized.

Flow cytometry is performed for quantitation of $CD4^+$ $CXCR3^+$ T cells from the conjunctiva and lacrimal gland. The tissues are teased and shaken at 37° C. for 60 minutes with 0.5 mg/mL collagenase type D. After grinding with a syringe plunder and passage through a cell strainer, cells are obtained, centrifuged, and resuspended in PBS with 1% bovine serum albumin. After washing, the samples are incubated with fluorescein-conjugated anti-CD4 antibody (BD Biosciences, San Jose, Calif.), phycoerythrin-conjugated anti-CXCR3 antibody (BD Biosciences), and isotype control antibody at 37° C. for 30 minutes. The number of $CD4^+CXCR3^+$ T cells is counted by a FACSCalibur cytometer with CellQuest software (BD Biosciences)

Statistical differences in the tear volume and corneal irregularity score results are evaluated by one-way ANOVA, with post hoc analysis. Kruskal-Wallis and Mann-Whitney test are used to compare the cytokine level, goblet cell density, and flow cytometry between groups. A p-value<0.05 is considered statistically significant.

Administration of adiponectin peptidomimetics described herein can increase tear volume, decrease severity of corneal surface irregularity, and/or decrease the number of inflammatory response cells in and around the eye in a mouse model of dry eye.

Example 3

Topical Administration of Adiponectin Peptidomimetics Improves Tear Production and Corneal Surface Irregularities Caused by Dry Eye This example illustrates the use of adiponectin peptidomimetics such as ADP355 and ADP399 to treat dry eye in a subject in need thereof. ADP355 has the sequence: DAsn-Ile-Pro-Nva-Leu-Tyr-DSer-Phe-Ala-DSer-NH$_2$ (SEQ ID NO:6). ADP399 is a linear branched dimer of ADP355 and has the sequence: (DAsn-Ile-Pro-Nva-Leu-Tyr-DSer-Phe-Ala-DSer-His-Pro)$_2$-Dab-NH$_2$ (SEQ ID NO:7). Nva refers to norvaline and Dab refers to 2,3-diamino butyric aicd. Detailed descriptions of ADP355 and ADP399 are found, for example, in U.S. Pat. No. 9,073,965 and Otvos et al., Frontiers in Chemistry, 2014, 2(93): 1-15, doi: 10.3386/fchem.2014.00093, the disclosures are hereby incorporated by reference in their entirety for all purposes.

Experimental dry eye (EDE) was induced in 8-week old female C57BL/6 mice by subcutaneous injection of 0.5 mg/0.2 mL scopolamine hydrobromide (Sigma-Aldrich, St. Louis, Mo.) three times a day (9 AM, 1:30 PM and 6 PM). A dose of 0.3 mL scopolamine hydrobromide was administered at each injection. The mice were also exposed to an air draft and 30% ambient humidity. 6 experimental groups used in this study included: (1) untreated control mice (UT; no dry eye treatment and no topical treatment); (2) untreated EDE control mice (EDE; received no topical administration); (3) EDE control mice received a balanced salt solution (BSS); (4) EDE mice received 0.01% single chain adiponectin peptidomimetic (ADP355) in BSS; (5) EDE mice receiving 0.01% peptide dimer adiponectin peptidomimetic (ADP399) in BSS; and (6) EDE mice receiving 0.01% recombinant globular adiponectin (gAdipo) in BSS. Each group included 5 mice. EDE mice treated with BSS received topical bilateral administration of 2 µi/eye, 3 times a day. EDE mice treated with ADP355 received topical bilateral administration of 2 µi/eye, 3 times a day. EDE mice treated with ADP-399 received topical bilateral administration of 2 µi/eye, 3 times a day. The gAdipo treated mice served as a positive treatment control. Mice were evaluated at baseline, day 5 and day 10 after the treatment initiation. In some experiments, ADP355, ADP-399 and gAdipo were resuspended in 0.01% BSA.

Tear volume was measured using a phenol red thread tear test. Briefly, a cotton thread treated with phenol red at its tip (Zone-Quick; Oasis, Glendora, Calif.) was held with jeweler's forceps and placed in the tear meniscus of the lateral canthus for 20 secs to contact tear fluid. Using a microscope, the length of the red portion (wet portion) of the thread was measured in millimeters. A standard curve was derived to convert the distance measurement into tear volume.

FIG. 1 shows that tear production, as measured by tear volume, was higher in adiponectin peptidomimetic treated EDE mice compared to untreated or BSS treated EDE mice (p-value<0.05 for ADP355 vs. EDE, p-value<0.05 for ADP399 vs. EDE). A statistically significant difference of tear volume was observed between the treated and untreated EDE mice. There was no significant difference in tear volume among those treated with ADP355, ADP399 and globular adiponectin. Tear volumes in all groups at day 10 after treatment initiation were similar to those at day 5.

Figure 2:
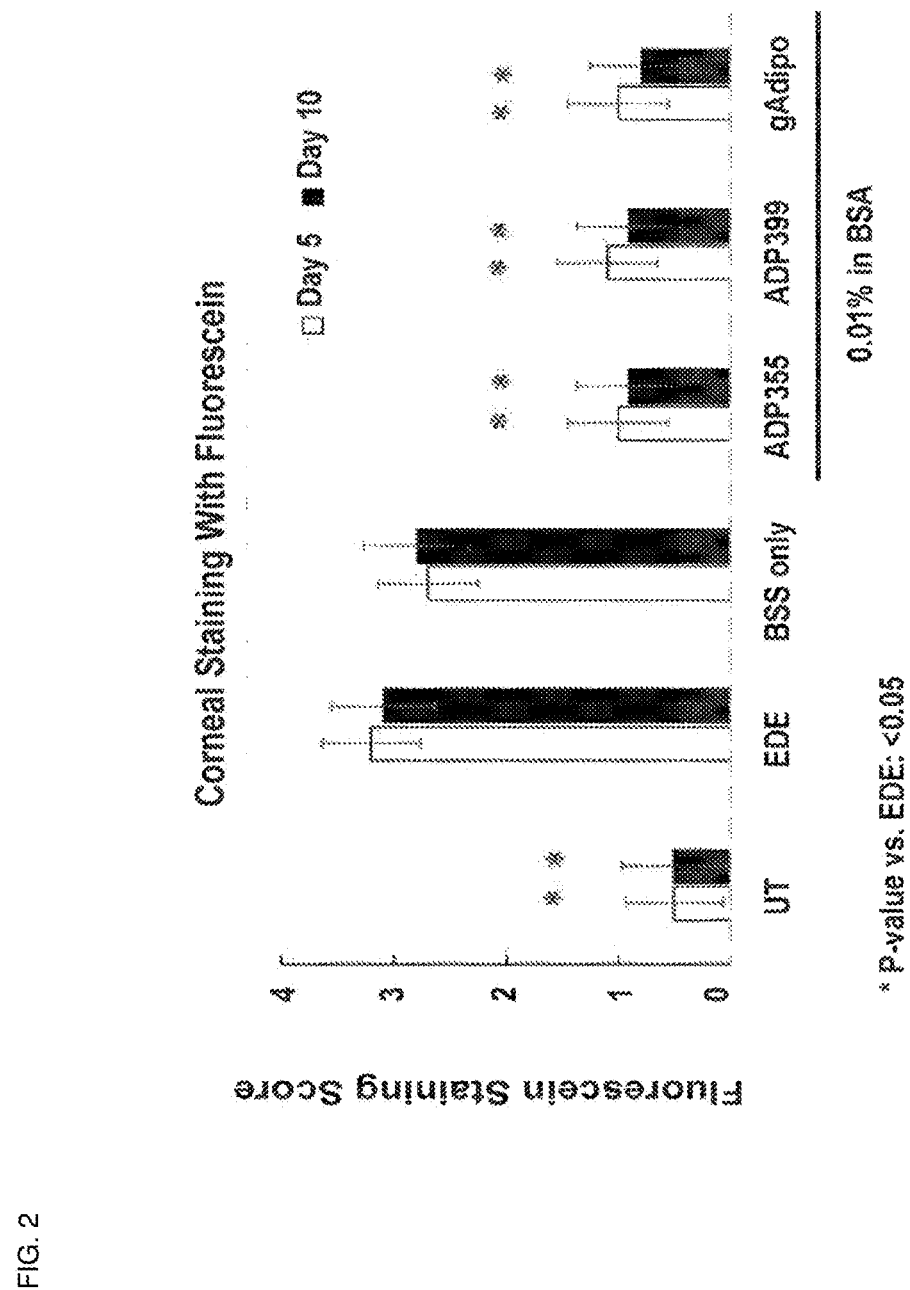
FIG. 2 shows that adiponectin peptidomimetic treatment minimized or decreased corneal surface irregularity in a mouse model of experimental dry eye, compared to control untreated EDE mice. Fluorescein staining was used to evaluate the smoothness of the corneal surface. The corneal surface was assessed at day 5 and day 10 after EDE initiation. "UT" represents untreated (normal) eye mice; "EDE" represents untreated experimental dry eye control mice; "BSS only" represents experimental dry eye mice treated with only balanced salt solution; "ADP355" represents experimental dry eye mice treated with adiponectin peptidomimetic; "ADP399" represents experimental dry eye mice treated with adiponectin peptidomimetic (linear branched dimer); and "gAdipo" represents experimental dry eye mice treated with recombinant murine full-length globular adiponectin.

The severity of corneal epithelial damage was evaluated by corneal fluorescein staining. Briefly, 1% fluorescein dye (1 µi) was instilled into the eye and then the eye was washed with saline. 10 minutes after application of the dye, the eye was photographed with a slip lamp microscope using a cobalt blue light. The stained area was graded using a scoring system by two blinded observers. Five different regions of the cornea (central, superior, inferior, nasal and temporal regions) were assessed according to a 0-4 score for each region: score 0 represents no or absent staining; score 1 represents punctate staining of less than 30 spots; score 2 represents punctate staining of greater than 30 spots but not diffuse; score 3 represents severe diffuse staining but not or absent positive plaque; and score 4 represents severe diffuse staining with positive fluorescent plaque. The average score from the five regions was recorded. FIG. 2 shows that EDE mice treated with an adiponectin peptidomimetic such as ADP355 and ADP-399 exhibited less corneal staining (less corneal irregularity) compared to untreated EDE mice (p-value<0.05 for ADP355 vs. EDE, p-value<0.05 for ADP-399 vs. EDE). A statistically significant improvement of the corneal fluorescent staining score was observed in the adiponectin peptidomimetic treated group compared to the untreated group. In addition, the adiponectin peptidomimetic-treated mice (ADP355 and ADP-399) had corneal surfaces that were similar to those of untreated normal mice (UT) and positive control globular adiponectin-treated mice (gAdipo). The corneal surface scores in all groups at day 10 were similar to those at day 5 after treatment initiation.

This study shows that topical administration of an adiponectin peptidomimetic reduced or eliminated a clinical sign of dry eye such as tear production and ocular surface irregularities. Administration of eye drops containing adiponectin peptidomimetics including single chain adiponectin peptidomimetics (e.g., ADP355) and peptide dimer adiponectin peptidomimetics (e.g., ADP399) had a beneficial effect on tear production and ocular surface of EDE. As such, topical application of adiponectin peptidomimetics to the eye can be useful for the treatment of dry eye in a subject in need thereof.

Example 4

Topical Administration of Adiponectin Peptidomimetics in Combination with 5% Lifitegrast Improves Tear Film Stability and Corneal Surface Irregularities Caused by Dry Eye This example illustrates the use of adiponectin peptidomimetics such as ADP355 in combination with 5% Lifitegrast to treat dry eye in a subject in need thereof. ADP355 has the sequence: DAsn-Ile-Pro-Nva-Leu-Tyr-DSer-Phe-Ala-DSer-NH$_2$ (SEQ ID NO:6). Lifitegrast is a prescription eye drop sold under the trade name Xiidra (Shire US Inc., Lexington, Mass.) as a 5% ophthalmic solution for topical ophthalmic use. A detailed description of ADP355 is found, for example, in U.S. Pat. No. 9,073,965 (ADP355), the disclosure is hereby incorporated by reference in its entirety for all purposes.

Experimental dry eye (EDE) was induced in 8-week old female C57BL/6 mice by subcutaneous injection of 0.5 mg/0.2 mL scopolamine hydrobromide (Sigma-Aldrich, St.

Louis, Mo.) three times a day (9 AM 0.3 mL, 1:30 PM 0.3 mL, and 6:00 PM 0.3 mL). The mice were also exposed to an air draft and 30% ambient humidity. Five experimental groups used in this study included: (1) untreated control mice (UT; no dry eye treatment and no topical treatment); (2) EDE control mice received a balanced salt solution (BSS); (3) EDE mice received ADP 355 0.1% (single chain adiponectin peptidomimetic (ADP 355) in BSS); (4) EDE mice received Lifitegrast 5%; and (5) EDE mice received 0.1% peptide adiponectin peptidomimetic (ADP 355) in BSS+Lifitegrast 5%. Each group included 5 mice. EDE mice treated with BSS, or 0.1% Adiponectin 355 alone or in combination with Lifitegrast 5%, received topical bilateral administration of BSS, or 0.1% Adiponectin 355, 2 µï/eye, 3 times a day. EDE mice treated with Lifitegrast 5%, alone or in combination with 0.1% Adiponectini355, received topical bilateral administration of Lifitegrast 5%, 2 µï/eye, 2 times a day. Mice were evaluated at baseline, day 5 and day 10 after the treatment initiation.

Experiment 1—Tear Film Break-up (BUT): This experiment evaluated the anti-inflammatory activity and efficacy of the ADP355 0.1% alone or in combination with Lifitegrast 5% in ameliorating Desiccation-induced Dry Eye (DED). Eyes were evaluated for time for dry spots to appear on the corneal surface of the eye after blinking. This assay provides a method to evaluate the tear film stabiliy as well as determining if evaoprative dry eye is present. The longer the time before tear film break-up indicates a more stable tear film. Subjects with normal tear quantity but an unstable tear film can explain dry eye symptoms. Tear instability can indicate an imbalance in tear composition causing tears to evaporate too fast or improper adhesion to the eye surface. Alternatively, insufficient lipid secretion by the melbomian glands due to melbomiam gland dysfunction can also cause tear film instability. Evaluations were done at five and 10 day enpoints with around >3-5 seconds a normal time. <2.2-3.0 seconds marginal and <2.2 seconds low and a high likelihood of dry eye symptoms and no discernable improvement in efficacy.

Figure 3A:
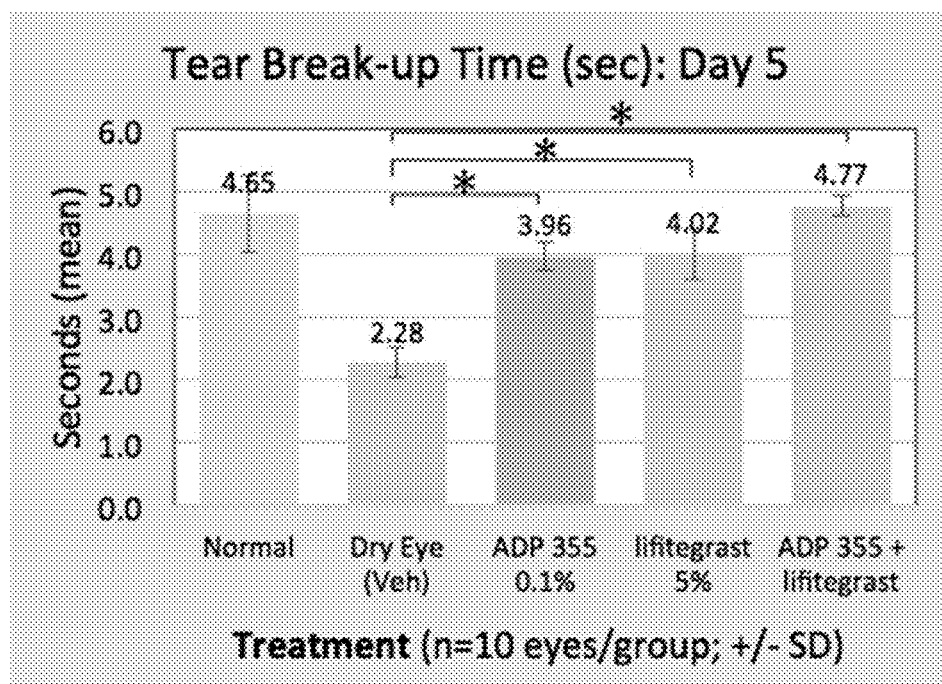
FIGS. 3A and 3B depict bar charts illustrating the change in tear film break-up time when dry eye is untreated, normal (UT) and treated with 0.1% ADP 355, 5% Lifitegrast, and both 0.1% ADP 355 +5% Lifitegrast.
Figure 3B:
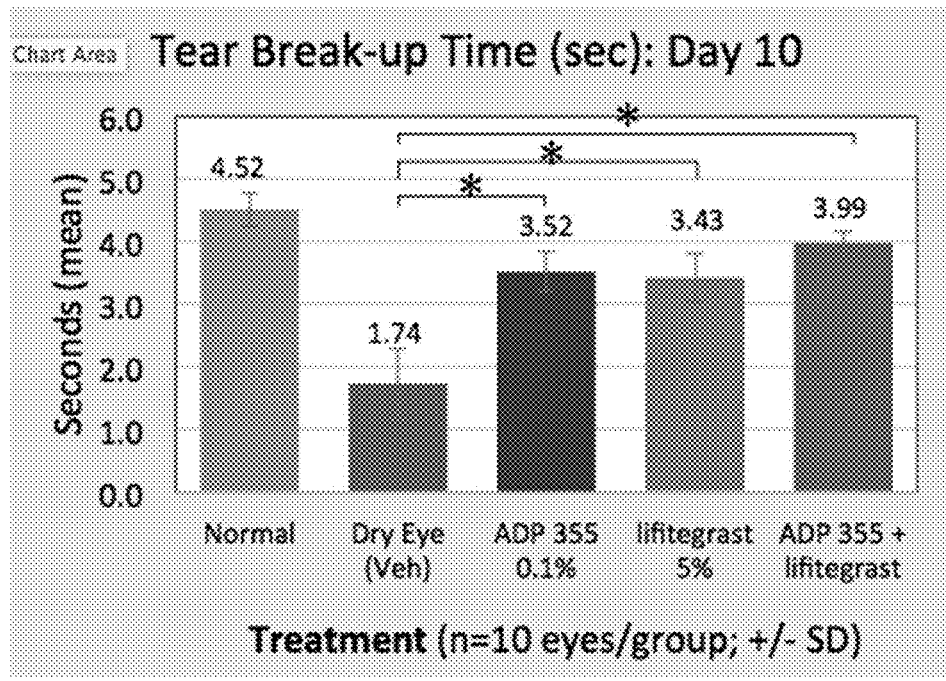

FIGS. 3A and 3B illustrate that tear production, as measured by tear film break-up time (BUT). BUT (stability), was longer in adiponectin peptidomimetic ADP 355+Lifitegrast 5% treated EDE mice compared to BSS treated EDE mice (p-value<0.05 for Groups 3-6). Group 5 (those treated with ADP355+Lifitegrast 5%) had a noticeable improvement in tear film times at both endpoints (around 4.8 seconds at D5 and 4.2 seconds at D10) compared to Groups 3 and 4 treated with either 0.1% Adiponectin 355, or with Lifitegrast 5% alone, respectively. Clearly there appeared to be an additive effect by treating with both ADP355 0.1%+Lifitegrast 5%.

Experiment 2—Corneal staining: The purpose of the corneal staining assay was to evaluate damage to the cornea epithelia in the murine EDE subject either as a consequence of inducing dry eye or due to treatment with 0.1% ADP 355 or with Lifitegrast 5% alone or with the combination of 0.1% ADP 355+Lifitegrast 5%. Fluorescein staining detects disruptions, changes in the contu e and detectable injury to the epithelium surface cells of the cornea. The lower the staining grade the less severe the corneal damage. Corneal staining was assessed in four quadrants using a 4-point scale with 16 being the maximum score.

Figure 4A:
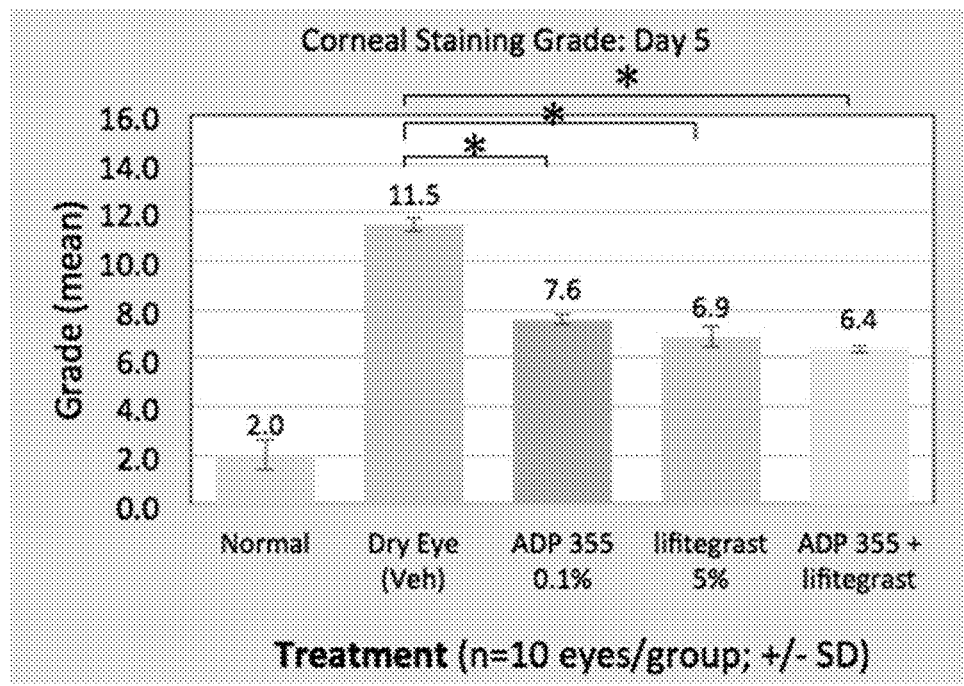
FIGS. 4A and 4B depict bar charts illustrating changes in corneal staining when dry eye is untreated, normal (UT) and treated with either 0.1% ADP 355, 5% Lifitegrast, and both 0.1% ADP 355+Lifitegrast 5%.
Figure 4B:
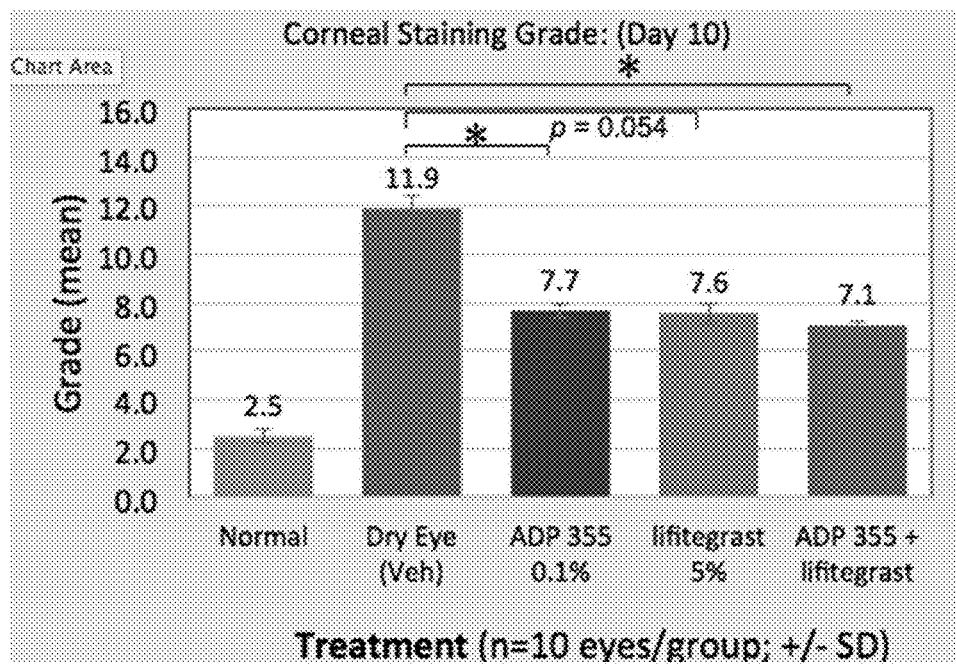

Briefly, fluorescein dye (1 µï) was instilled into the eye and then the eye was washed with saline. 10 minutes after application of the dye, the eye was photographed with a slip lamp microscope using a cobalt blue light. The stained area was graded using a scoring system by two blinded observers. Five different regions of the cornea (central, superior, inferior, nasal and temporal regions) were assessed according to a 0-4 score for each region: score 0 represents no or absent staining; score 1 represents slightly punctate staining of less than 30 spots; score 2 represents punctate staining of greater than 30 spots but not diffuse; score 3 represents severe diffuse staining but no or absent positive plaque; and score 4 represents severe diffuse staining with positive fluorescein plaque. The average score from the five regions was recorded. FIGS. 4A and 4B illustrate grading of the staining results at D5 and D10, respectively. Again, as in the tear film break-up study, treated eyes had a lower grade than the untreated eyes (Group 2, BSS). Treatment with either ADP 355 0.1%, or Lifitegrast 5% improved corneal disruptions resulting from induced dry eye. However, greater improvement was most noticeable at D5 (FIG. 4A) in EDE eyes treatment with both 0.1% ADP 355+Lifitegrast 5%. At D10 (FIG. 4B), the combination was only slightly better than any of single treatments alone and each treatment still had a lower grade than the untreated dry eyes.

Experiment 3—Flow Cytometry: The purpose of this test was to quantify the presence of CD4+ and CCR5+ T cells from the conjunctiva and lacrimal gland as previously described (Yoon K C, Heo H, Kang I S, et al. Cornea (2008) 27: 454-460). High levels of inflammatory cells is indicative of ocular inflammation. The tissues are teased and shaken at 37° C. for 60 minutes with 0.5 mg/mL collagenase type D.

Figure 5A:
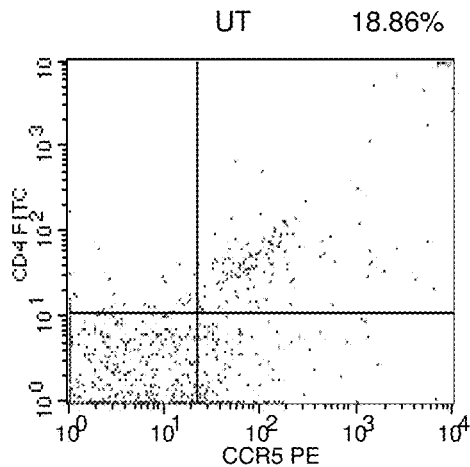
FIG. 5A represents scatter plots of activated T cell level of normal (UT) eye. After treatment, the changes in activated T cell levels are illustrated in scatter plots of FIG. 5C (after administration of 0.1% ADP 355), FIG. 5D (after administration of 5% Lifitegrast), and FIG. 5E (after administration of both 0.1% ADP 355+Lifitegrast 5%).
Figure 5B:
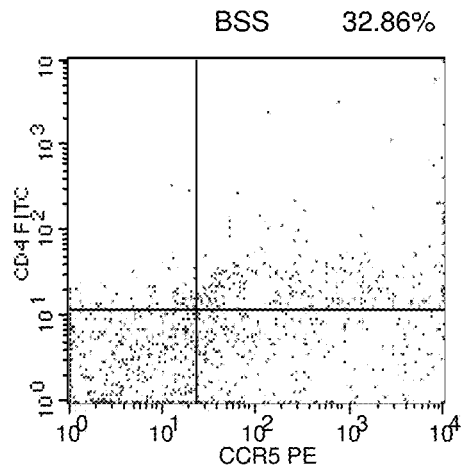
FIG. 5B depicts scatter plots illustrating the change in Activated T cell levels when dry eye presents as conjunctiva.
Figure 5C:
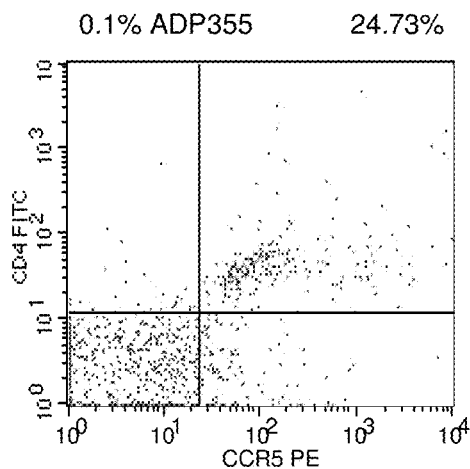
Figure 5D:
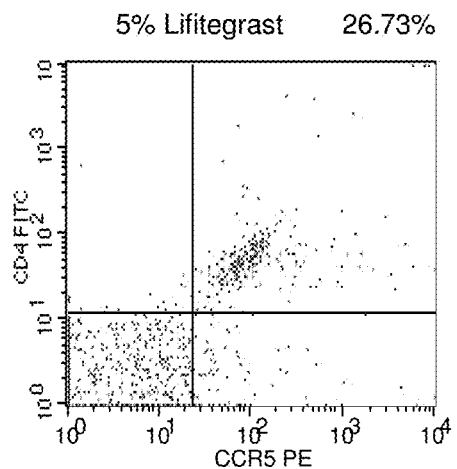
Figure 5E:
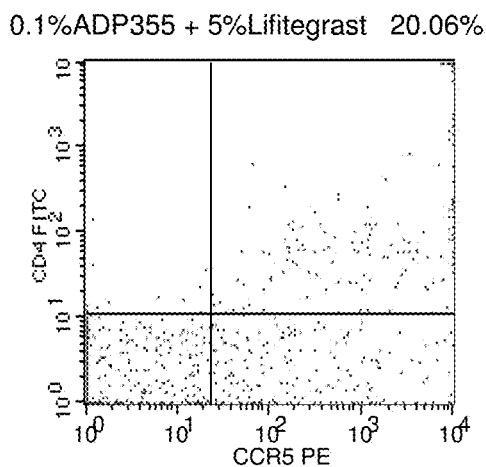

After grinding with a syringe plunder and passage through a cell strainer, cells are obtained, centrifuged, and resuspended in PBS with 1% bovine serum albumin. After washing, the samples are incubated with fluorescein-conjugated anti-CD4 antibody (BD Biosciences, San Jose, Calif.), phycoerythrin-conjugated anti-CC5+R antibody (BD Biosciences), and isotype control antibody at 37° C. for 30 minutes. The number of $CD4^+$ and $CCR5^+$ T cells is counted by a FACSCalibur cytometer with CellQuest software (BD Biosciences). Results for each treatment group are presented in FIGS. 5A-5E and 6A-6E. The results indicate that after 10 days only 0.1% ADP 355+Lifitegrast 5% restablished Activated T Cell levels within the normal range as the percentage was 20.06% with the control at 28.86% in the conjunctiva (FIGS. 5E and 5A, respectively) 12.53% with the control at 11.09% in the lacrimal gland (FIGS. 6E and 6A, respectively).

Experiment 4—Cytokine Assessment

The purpose of this experiment is to identify and assess the presence of cytokines in the conjunctive and lacrimal gland of mice with and without EDE.

A multiplex immunobead assay (Luminex 200; Luminex Corp., Austin, Tex.) is used to measure the concentrations of IFN-γ, IL-1B, MIP1B, TNF-α, IL-6, IFN-c, and monokine induced by interferon-c (MIG) in the conjunctiva and lacrimal gland. The tissues are collected and pooled in lysis buffer containing protease inhibitors for 30 minutes. The cell extracts are centrifuged at 14,000 g for 15 minutes at 48° C., and the supernatants were stored at −70° C. before use. The supernatants are added to wells containing the appropriate cytokine bead mixture that include mouse monoclonal antibodies specific for IFN-γ, IL-1B, MIP1B, TNF-α, IL-6, IFN-c, and MIG for 60 minutes. After three washes with assay buffer, the biotinylated secondary cytokine antibody mixture is applied for 30 minutes in the dark at room temperature. The reactions are detected after addition of streptavidin-phycoerythrin with an analysis system (xPONENT, Austin, Tex.). The concentrations of these factors in tissue are calculated from standard curves of known concentrations of recombinant mouse cytokines.

Eye and adnexa are surgically excised, fixed in 4% paraformaldehyde, and embedded in paraffin. Six-micrometer sections are stained with periodic acid-Schiff (PAS) reagent. Sections are examined and photographed with a microscope (BX53; Olympus, Tokyo, Japan) equipped with a digital camera (F2; Foculus, Finning, Germany). Goblet cell density in the superior and inferior conjunctiva are measured in three sections from each eye using image analysis software (Media Cybernetics, Silver Spring, Md.) and expressed as the number of goblet cells per fixed area. Immunohistochemistry is performed to detect the expression of adiponectin receptors, AdipoRI and AdipoR2, in the conjunctiva of normal eyes and TNF-a in the conjunctiva and lacrimal gland of experimental dry eyes. Hydrogen peroxide ($H_2O_2$, 0.3%) in phosphate buffered saline (PBS) and 20% serum in PBS are sequentially applied to the sections. Conjunctival sections from UT control mice are incubated with goat anti-adiponectin receptor AdipoRI and AdipoR2 antibodies (Vector Laboratories, Burlingame, Calif.). Conjunctival and lacrimal gland sections from mice with EDE are incubated with goat monoclonal anti-mouse TNF-a antibody (Santa Cruz Biotechnology, Santa Cruz, Calif.). After washing, appropriate secondary antibodies are applied. The samples are incubated with avidin-peroxidase, then incubated with 3,30-diaminobenzidine peroxidase substrate and counterstained with Mayer's hematoxylin.

FIG. 7 illustrates cytokine levels in conjunctiva and lacrimal glands following treatment with a BSS, 0.1% ADP 355, Lifitegrast 5% or 0.1% ADP 355+administration of Lifitegrast 5%. Readily evident is the decreased level of cytokines resulting from treatment with administration of both 0.1% ADP 355+Lifitegrast 5%, providing improved efficacy of the combined treatment.

Statistical differences in the tear break-up time, corneal staining and normal score results were evaluated by one-way ANOVA, with post hoc analysis. Kruskal-Wallis and Mann-Whitney test were used to compare flow cytometry between groups. A P value<0.05 was considered statistically significant.

This study shows that topical administration of an adiponectin peptidomimetic, 0.1% ADP 355+ administration of Lifitegrast 5% improved tear film stability and eliminated a clinical sign of dry eye such as ocular surface irregularities and decreased the number of inflammatory response cells in and around the eye in a mouse model of dry eye when compared to topical administration of either 0.1% ADP 355, or Lifitegrast 5% alone. As such, topical application of an adiponectin peptidomimetic(s)+Lifitegrast 5% to the eye appears to have improved efficacy and can be useful for the treatment of dry eye in a subject in need thereof.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for treating dry eye in a subject in need thereof, the method comprising administering to the subject a therapeutically effective amount of a composition comprising: an adiponectin peptidomimetic compound, Lifitegrast and a pharmaceutically acceptable carrier, to treat dry eye in the subject, wherein the adiponectin peptidomimetic compound is represented by Formula II: $Xaa_i$-Ile-Pro-$Xaa_2$-Leu-Tyr-$Xaa_3$-Phe-Ala-$Xaa_4$-$Xaa_5$ (SEQ ID NO:1), wherein $Xaa_i$ is Asn or a non-natural amino acid, $Xaa_2$ is Gly or a non-natural amino acid, $Xaa_3$ is Tyr or a non-natural amino acid, $Xaa_4$ is Tyr or a non-natural amino acid, and $Xaa_5$ is no amino acid, β-Ala or P-Ala-$NH_2$, wherein the C-terminal amino acid is optionally amidated, or a pharmaceutically acceptable salt thereof.

2. The method of claim 1, wherein the composition is administered topically, by intravitreal injection, by subconjunctival injection, by conjunctival injection, by intramuscular injection, by subcutaneous injection, by intravenous injection, by intracameral injection, or by implantation into the subject's eye.

3. The method of claim 1, wherein the dry eye is selected from the group consisting of hypolacrimation, tear deficiency, xerophthalmia, Sjogren's syndrome dry eye, non-Sjogren's syndrome dry eye, keratoconjuctivitis sicca, aqueous tear- deficiency dry eye (ADDE), evaporative dry eye (EDE), environmental dry eye, Stevens- Johnson syndrome, ocular pemphigoid blepharitis marginal, eyelid-closure failure, sensory nerve paralysis, allergic conjunctivitis-associated dry eye, post- viral conjunctivitis dry eye, postcataract surgery dry eye, VDT operation- associated dry eye, and contact lens wearing- associated dry eye.

4. The method of claim 1, wherein the composition is administered to the subject once a day, two times a day, three times a day, four time a day or more often.

5. The method of claim 1, wherein the composition is administered to the subject once a day, two times a day, three times a day, four time a day or more often.

6. The method of claim 1, wherein the composition is administered every other day or less often.

7. The method of claim 1, wherein the composition is administered every other day or less often.

8. The method of claim 1, wherein the adiponectin peptidomimetic compound is present in an amount between 0.0001% (wt) to 90% (wt) of the composition.

9. The method of claim 1, wherein the composition is administered in an amount between 0.1% (wt) to 20% (wt) of the composition.

10. The method of claim 1, wherein the composition is in a formulation selected from the group consisting of a solution, suspension, syrup, liquid, gel, hydrogel, emulsion, liposome, aerosol, mist, film, suspension, plug, polymer, implant, contact lens, ocular insert, nanoparticle, microparticle, a sustained release formulation, and a formulation suitable for an ocular medical device.

11. The method of claim 1, further comprising administering a composition comprising cyclosporine, artificial tears, a corticosteroid, an anti-inflammatory agent, or any combination thereof.

12. The method of claim 1, wherein the adiponectin peptidomimetic compound is selected from the group consisting of D- Asn-Ile-Pro-Nva-Leu-Tyr-D-Ser-Phe-Ala-D-Ser (SEQ ID NO:3), D-Asn- Ile-Pro-Nva-Leu-Tyr-D-Ser-Phe-Ala-DSer-p-Ala (SEQ ID NO:4), D-Asn- Ile-Pro-Nva-Leu-Tyr-D-Ser-Phe-Ala-D-Serp-Ala-NH2(SEQ ID NO:5), D- Asn-Ile-Pro-Nva-Leu-Tyr-D-Ser-Phe-Ala-D-Ser-NH2 (SEQ ID NO:6), (D-Asn-Ile-Pro- Nva-Leu-Tyr-D-Ser-Phe-Ala-D-Ser-His-Pro)$_2$-Dab- NH2(SEQ ID NO:7), a variant thereof, a derivative thereof, and a pharmaceutically acceptable salt thereof.

13. The method of claim 1, wherein the adiponectin peptidomimetic compound is SEQ ID NO:6.

14. The method of claim 1, wherein the composition further comprises a therapeutic agent which is a cyclosporine ophthalmic emulsion.

15. The method of claim 14, wherein the therapeutic agent comprises 3.5% to 6.5% Lifitegrast or a pharmaceutically acceptable salt thereof.

16. The method of claim 1, wherein the subject presents at least one symptom or clinical sign of dry eye selected from the group consisting of a change in tear secretion, a change in tear clearance, ocular surface damage, corneal epithelial defects, a change in ocular surface cells, a change in tear film stability, a change in tear volume, a change in tear film composition, a change in tear osmolarity, and any combination thereof.

* * * * *